US007773760B2

(12) United States Patent
Sakamoto et al.

(10) Patent No.: US 7,773,760 B2
(45) Date of Patent: Aug. 10, 2010

(54) ACTIVE VIBRATIONAL NOISE CONTROL APPARATUS

(75) Inventors: Kosuke Sakamoto, Utsunomiya (JP); Toshio Inoue, Tochigi-ken (JP); Akira Takahashi, Tochigi-ken (JP); Yasunori Kobayashi, Utsunomiya (JP)

(73) Assignee: Honda Motor Co., Ltd., Tokyo (JP)

( * ) Notice: Subject to any disclaimer, the term of this patent is extended or adjusted under 35 U.S.C. 154(b) by 924 days.

(21) Appl. No.: 11/605,238

(22) Filed: Nov. 29, 2006

(65) Prior Publication Data

US 2007/0140503 A1 Jun. 21, 2007

(30) Foreign Application Priority Data

Dec. 16, 2005 (JP) ............................ 2005-363496

(51) Int. Cl.
*H03B 29/00* (2006.01)
*G10K 11/16* (2006.01)
*A61F 11/06* (2006.01)

(52) U.S. Cl. ................. 381/71.9; 381/71.14; 381/71.4; 381/71.8; 381/86

(58) Field of Classification Search ..... 381/71.1–71.14, 381/86, 94.1–94.3; 181/206
See application file for complete search history.

(56) References Cited

U.S. PATENT DOCUMENTS 4,506,380 A * 3/1985 Matsui ...................... 381/71.9
5,426,703 A * 6/1995 Hamabe et al. .......... 381/71.12
5,581,619 A * 12/1996 Shibata et al. ............ 381/71.4
6,002,778 A * 12/1999 Rossetti et al. ............ 381/71.4
6,650,756 B1 * 11/2003 Saito et al. ............... 381/71.12
7,340,065 B2 * 3/2008 Nakamura et al. ....... 381/71.11
7,352,869 B2 * 4/2008 Inoue et al. .............. 381/71.11
7,574,006 B2 * 8/2009 Funayama et al. ....... 381/71.12
7,633,257 B2 * 12/2009 Sakamoto et al. ........... 318/611
2008/0192948 A1 * 8/2008 Kan et al. ................. 381/71.4

FOREIGN PATENT DOCUMENTS

JP 03-005255 A 1/1991
JP 07-064575 A 3/1995

* cited by examiner

*Primary Examiner*—Xu Mei
(74) *Attorney, Agent, or Firm*—Arent Fox LLP

(57) ABSTRACT

While a vehicle incorporating an active vibration noise control apparatus is decelerating, hysteresis is given if an operating point moves from an operating point on a sampling period characteristic curve to an operating point on another sampling period characteristic curve. Even if a base period detected depending on noise contains fluctuations, a smooth noise control process is performed. Since a division number produced when the base period is divided by a sampling period is a real number, the freedom of design is widened. Less strict limits are posed on the processing capability of a CPU of the active vibration noise control apparatus to provide a wider control range.

10 Claims, 17 Drawing Sheets

| ADDRESS | WAVEFORM DATA |
|---|---|
| 0 | 0 |
| 1 | $A\sin(360° \times \frac{1}{N})$ |
| ⋮ | ⋮ |
| i | $A\sin(360° \times \frac{i}{N})$ |
| ⋮ | ⋮ |
| N-1 | $A\sin(360° \times \frac{N-1}{N})$ |

ACTIVE VIBRATIONAL NOISE CONTROL APPARATUS

BACKGROUND OF THE INVENTION

1. Field of the Invention

The present invention relates to an active vibrational noise control apparatus for actively controlling vibrational noise with adaptive notch filters, and more particularly to an active vibrational noise control apparatus for use on vehicles.

2. Description of the Related Art

FIG. 15 of the accompanying drawings shows in block form an electric arrangement of a general active vibrational noise control apparatus 1 for actively controlling vibrational noise with an adaptive notch filter.

As shown in FIG. 15, the active vibrational noise control apparatus, generally denoted by 1, has an adaptive notch filter 2 and a reference signal generator 3 which are supplied with a base signal x(n) generated from the frequency of vibrational noise that is to be controlled.

The reference signal generator 3 generates and outputs a reference signal r(n) which takes into account transfer characteristics from a speaker 4 serving as a control sound source to a microphone 5 which outputs a residual noise signal e(n).

A filter coefficient updater 6 calculates and sequentially updates a filter coefficient W(n) of the adaptive notch filter 2 from the reference signal r(n) and the residual noise signal e(n) according to the equation [$W(n+1)=W(n)+\mu e(n)\cdot r(n)$: μ represents a constant] in order to minimize the residual noise signal e(n).

The adaptive notch filter 2 outputs a control signal $y(n)=x(n)W(n)$ based on the filter coefficient W(n) and the base signal x(n).

In the active vibrational noise control apparatus 1, the base signal x(n), the filter coefficient W(n+1), the residual noise signal e(n), and the control signal y(n), etc. are generated or detected in each sampling period.

It is assumed that the fixed sampling technology with a fixed sampling period is employed, and the active vibrational noise control apparatus 1 has a control range (base signal frequency range) from 0 [Hz] to 1000 [Hz], for example, in which the base signal x(n) is generated with a resolution of 0.1 [Hz].

At a fixed sampling frequency of 4000 [Hz] (fixed sampling period of 0.25 [ms]), the active vibrational noise control apparatus 1 requires a data table (a storage means such as a memory) for storing discrete 40000 (=sampling frequency/resolution=4000/0.1) waveform data for generating the base signal x(n). Therefore, the active vibrational noise control apparatus 1 requires a storage means of large storage capacity and is costly to manufacture.

According to the conventional variable sampling technology with a sampling period being variable in synchronism with an engine rotational speed, if the number of discrete waveform data for generating the base signal x(n) is N, then in order to generate a base signal having a frequency in synchronism with the engine rotational speed, a sampling period ts (ts=Tnep/N) is calculated by dividing the period (base period Tnep) of engine pulses Pne in synchronism with the engine rotational speed by N, as shown in FIG. 16 of the accompanying drawings.

The base signal x(n) shown in a lower portion of FIG. 16 is generated depending on the sampling period ts.

According to the variable sampling technology, as the frequency of the base signal is lower, the number of noise canceling processes per second (=the number of updating processes or the number of calculations) is smaller. Consequently, the noise canceling capability varies in the control range. Since the number of discrete waveform data for generating the base signal x(n) is smaller than the number of discrete waveform data according to the fixed sampling technology, the storage means for storing the base signal may be of a smaller storage capacity. The number of discrete waveform data disclosed in Japanese Laid-Open Patent Publication No. 3-5255 is 180.

Noise control apparatus related to the variable sampling technology are disclosed in Japanese Laid-Open Patent Publication No. 3-5255 and Japanese Laid-Open Patent Publication No. 7-64575.

FIG. 17 of the accompanying drawings is a graph showing a control range according to the conventional variable sampling technology, the graph having a horizontal axis representative of the base period Tnep which is the base period of the base signal and a vertical axis representative of the sampling period ts. If the value produced by dividing the base period Tnep by the sampling period ts is referred to as a division number, then the division number is equal to the number of waveform data (N). Therefore, the sampling period ts can be determined as ts=Tnep/N from the base period Tnep along a sampling period curve C6 (C6=1/N) indicated by the thick solid line. Because as the base period Tnep is smaller, the sampling period ts is shorter, there is a trade-off problem between a sampling period tmin (=shortest sampling period=processing ability limit sampling period=lower limit sampling period) corresponding to the processing ability limit of a CPU of a microcomputer or the like and a base period Tnepmin (=base signal minimum period=base signal maximum frequency=maximum control frequency) at the lower limit of the control range.

In FIG. 17, tmax represents an upper limit sampling period (=longest sampling period=noise canceling ability limit sampling period) for achieving an effective noise canceling ability. If the sampling period ts is longer than the noise canceling ability limit sampling period tmax, then the number of noise canceling processes per second is so small that no desired noise canceling capability is available. In FIG. 17, Tnepmax represents an upper limit period (upper limit base period) of the base signal.

For performing effective noise control, it is necessary to equalize the minimum period of the base signal (lower limit base period) Tnepmin to the CPU processing ability limit sampling period (lower limit sampling period) and also to equalize the maximum period of the base signal (upper limit base period) Tnepmax to the noise canceling ability limit sampling period (upper limit sampling period) tmax. Therefore, if the control range is to be widened, then a fast high-performance CPU is needed, making the active vibrational noise control apparatus highly costly to manufacture.

The conventional variable sampling technology is also problematic in that since the number of waveform data and the division number are equal to each other, the number of waveform data and the division number N are a natural number, and the freedom with which to design the active vibration noise control apparatus is small.

SUMMARY OF THE INVENTION

It is an object of the present invention to provide an active vibration noise control apparatus which can be designed with increased freedom and poses much less strict limits of the processing ability of a CPU for achieving a wider control range.

Another object of the present invention is to provide an active vibration noise control apparatus which is capable of performing a vibration noise control process for a smooth noise canceling capability even when the engine rotational speed of an engine mounted on a vehicle which incorporates the active vibration noise control apparatus fluctuates due to an unconscious small action made by the user on the accelerator pedal for driving the vehicle at a constant speed, and as a result the base period of a base signal generated depending on engine vibrational noise contains a fluctuation.

According to the present invention, there is provided an active vibration noise control apparatus comprising a control sound source for generating control sound in a space in which noise is transmitted from a noise source, frequency detecting means for detecting a noise generating state of the noise source and outputting a harmonic base frequency selected from frequencies of the noise generated by the noise source and a base period corresponding to the base frequency, residual noise detecting means for detecting residual noise at a predetermined position in the space, and active control means for driving the control sound source to reduce the noise in the space based on a base signal and the residual noise.

The active control means comprises a waveform data table for storing waveform data of a sine wave or a cosine wave discretized into a predetermined number of values, sampling period calculating means for calculating a sampling period based on the base period, and base signal generating means for reading the waveform data from the waveform data table and generating the base signal.

The sampling period calculating means uses the base period of a particular base signal in a control range as an upper limit base period, and determines a division number which is a value produced when the upper limit base period is divided by an upper limit sampling period which is necessary for the active control means to provide a noise canceling capability, uses a period produced when a lower limit sampling period which is a limit of a processing capability of the active control means is multiplied by the division number, as an identical division number lower limit base period, and if the base period of the base signal is present in a range between the upper limit base period and the identical division number lower limit base period, outputs a value produced when the base period of the base signal is divided by the division number as the sampling period.

The base signal generating means uses the quotient produced when the predetermined number is divided by the division number or the sum of the quotient and 1 as a step number, and reads the waveform data from the waveform data table for each the step number in a sampling period which is of a value produced when the base period of the base signal is divided by the division number, thereby to generate the base signal.

Since the step number for reading the waveform data discretely is represented by a quotient produced when the predetermined number which is the total number of the waveform data is divided by the division number or the sum of the quotient and 1, the division number used in the variable sampling technology is not limited to only a natural number as with the prior art, but may be a real number, allowing a control range to be designed with increased freedom. Stated otherwise, using a real number as the division number makes it possible to set the upper limit sampling period as a noise canceling ability limit sampling period or the lower limit sampling period as a processing ability limit sampling period to a sampling period as a requisite minimum.

A harmonic generally signifies a frequency represented by an integral multiple of a fundamental. According to the present invention, a harmonic may also signify a frequency represented by a non-integral multiple, e.g., 1.5 times, 2.5 times, or the like.

The base period of the particular base signal may comprise a longest base period in the control range or a shorter period.

If the control range is wider than a range from the identical division number lower limit base period to the upper limit base period and has a lower limit base period smaller than the identical division number lower limit base period, the sampling period calculating means uses the identical division number lower limit base period as a second upper limit base period, determines a second division number which is of a value produced when the second upper limit base period is divided by the upper limit sampling period, uses a period produced when the lower limit sampling period is multiplied by the second division number as a second identical division number lower limit base period, and outputs a value produced when the base period of the base signal is divided by the second division number as a second sampling period if the base period of the base signal is present in a range between the second upper limit base period and the second identical division number lower limit base period. The base signal generating means uses the quotient produced when the predetermined number is divided by the second division number or the sum of the quotient and 1 as a second step number, and reads the waveform data from the waveform data table for each the second step number in the second sampling period, thereby to generate the base signal, if the base period of the base signal is present in a second range between the second upper limit base period and the second identical division number lower limit base period.

With the above arrangement, because the division number as a real number is changed in the control range to calculate the sampling period, the freedom of design is increased. As a result, less strict limits are posed on the processing ability of a CPU for achieving a wider control range.

More specifically, if the base period of the base signal is shorter, the division number is smaller than that of the longer base period of the base signal. Therefore, much less strict limits are posed on the processing ability of a CPU for achieving a wider control range in a shorter base period range.

Since the division number is a real number, the first identical division number lower limit base period and the second upper limit base period are necessarily of the same value.

The sampling period calculating means uses the base period of a particular base signal between the upper limit base period and the identical division number lower limit base period as a third upper limit base period, determines a third division number which is of a value produced when the third upper limit base period is divided by the upper limit sampling period, uses a period produced when the lower limit sampling period is multiplied by the third division number as a third identical division number lower limit base period, and outputs a value produced when the base period of the base signal is divided by the third division number as a third sampling period if the base period of the base signal is present in a range between the third upper limit base period and the third identical division number lower limit base period. The base signal generating means uses the quotient produced when the predetermined number is divided by the third division number or the sum of the quotient and 1 as a third step number, and reads the waveform data from the waveform data table for each the third step number in the third sampling period, thereby to generate the base signal, if the base period of the base signal is present in a third range between the third upper limit base period and the third identical division number lower limit base period. When the base period of the base signal changes to a smaller value, if the base period becomes smaller than the identical division number lower limit base period, then the sampling period calculating means changes from the sampling period to the third sampling period and outputs the third sampling period, and if the base period becomes smaller than the third identical division number lower limit base period, then the sampling period calculating means changes from the third sampling period to the second sampling period and outputs the second sampling period, and when the base period of the base signal changes to a greater value, if the base period becomes greater than the second upper limit base period, then the sampling period calculating means changes from the second sampling period to the third sampling period and outputs the third sampling period, and if the base period becomes greater than the third upper limit base period, then the sampling period calculating means changes from the third sampling period to the sampling period and outputs the sampling period.

With the above arrangement, even if the base period of the base signal generated depending on noise contains fluctuations, since hysteresis is given when the division number is changed, it is possible to perform a noise control process for a smooth noise canceling capability.

If the control range is wider than a range from the identical division number lower limit base period to the upper limit base period and has a lower limit base period smaller than the identical division number lower limit base period, the sampling period calculating means uses the base period of a particular base signal which is smaller than the upper limit base period and greater than the identical division number lower limit base period as a second upper limit base period, determines a second division number which is of a value produced when the second upper limit base period is divided by the upper limit sampling period, uses a period produced when the lower limit sampling period is multiplied by the second division number as a second identical division number lower limit base period, and outputs a value produced when the base period of the base signal is divided by the second division number as a second sampling period if the base period of the base signal is present in a range between the second upper limit base period and the second identical division number lower limit base period, and the base signal generating means uses the quotient produced when the predetermined number is divided by the second division number or the sum of the quotient and 1 as a second step number, and reads the waveform data from the waveform data table for each the second step number in the second sampling period, thereby to generate the base signal, if the base period of the base signal is present in a second range between the second upper limit base period and the second identical division number lower limit base period.

With this arrangement, the control range can be widened without having to shorten the processing ability limit sampling period.

When the base period of the base signal changes to a smaller value, if the base period becomes smaller than the identical division number lower limit base period, then the sampling period calculating means changes from the sampling period to the second sampling period and outputs the second sampling period, and when the base period of the base signal changes to a greater value, if the base period becomes greater than the second upper limit base period, then the sampling period calculating means changes from the second sampling period to the sampling period and outputs the sampling period.

With the above arrangement, even if the base period of the base signal generated depending on noise contains fluctuations, since hysteresis is given when the division number is changed, it is possible to perform a noise control process for a smooth noise canceling capability.

According to the present invention, less strict limits are posed on the processing ability of the CPU for a wider control range. As a result, an inexpensive CPU may be employed to reduce the cost of the active vibration noise control apparatus.

Inasmuch as a real number is used as the division number, the active vibration noise control apparatus can be designed with increased freedom.

Furthermore, even if the base period of the base signal generated depending on noise contains fluctuations, it is possible to perform a noise control process for a smooth noise canceling capability.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

An active vibration noise control apparatus according to the present invention will be described below.

Figure 1:
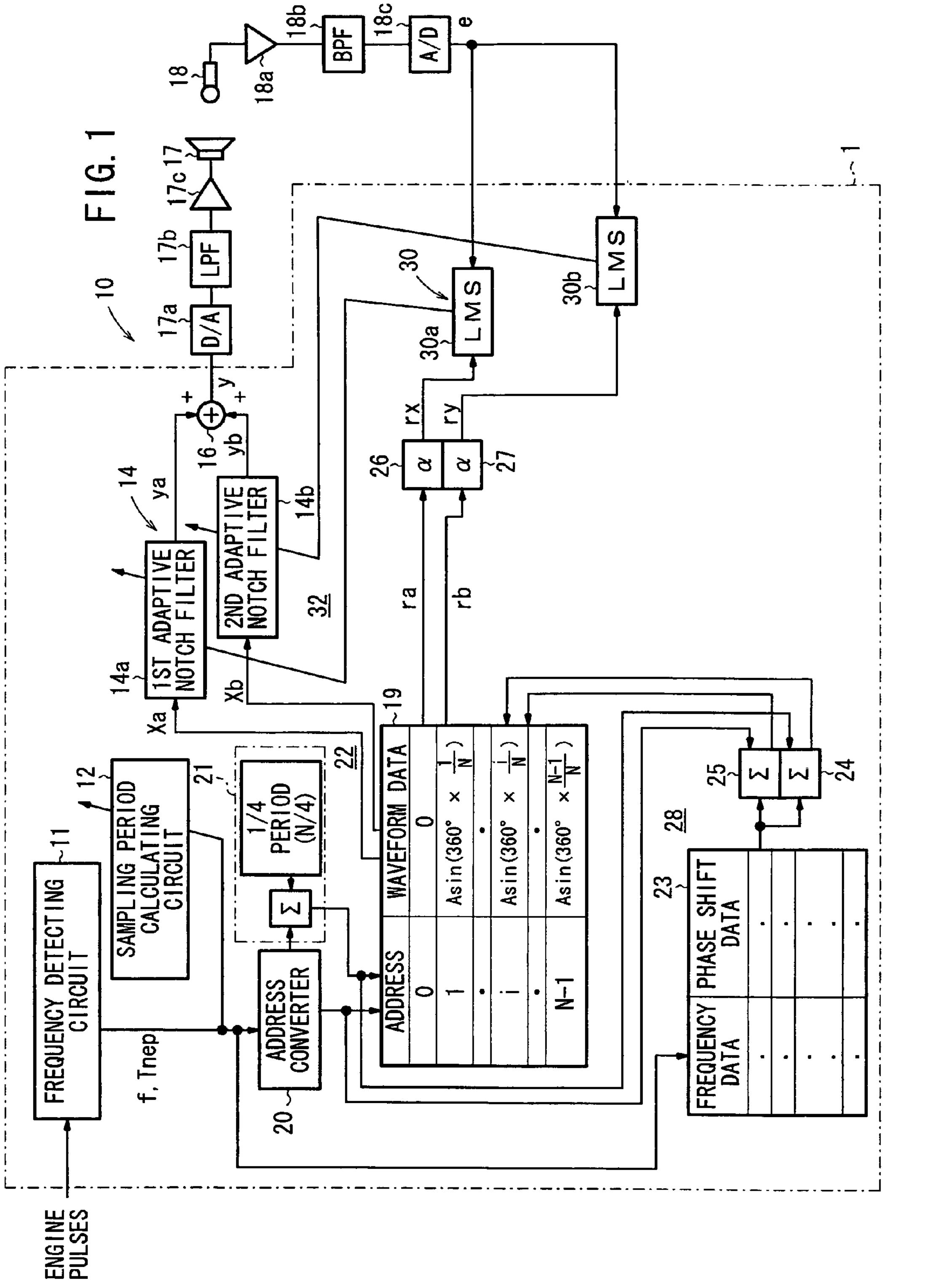
FIG. 1 is a block diagram of an active vibration noise control apparatus according to an embodiment of the present invention.

FIG. 1 shows in block form an arrangement of an active vibration noise control apparatus 10 according to an embodiment of the present invention.

The active vibration noise control apparatus 10 will be described below in an application for canceling noise including the muffled sound of an engine which is prevalent noise in the passenger compartment of a vehicle which incorporates the active vibration noise control apparatus 10.

The active vibration noise control apparatus 10 has its major part constructed in the form of a microcomputer 1 including a CPU, not shown. The CPU of the microcomputer 1 operates as various functional means by executing a program stored in a memory, not shown.

Basically, the microcomputer 1 has a base signal generating means 22 for generating a base signal X (a base cosine-wave signal Xa and a base sine-wave signal Xb) which is a harmonic of an engine rotational speed, by referring to engine pulses, a referenced signal generating means 28 for generating a reference signal r (a first reference signal rx calculated based on the base cosine-wave signal Xa and a second reference signal ry calculated based on the base sine-wave signal Xb) taking into account transfer characteristics from a speaker 17 serving as a control sound source to a microphone 18 which outputs a residual noise signal e, and an active control means 32 functioning as a control signal generating means for generating a control signal y (a control signal ya and a control signal yb) for driving the speaker 17, based on the base signal X, the reference signal r, and the residual noise signal e.

In the active vibration noise control apparatus 10, the rotation of the engine output shaft is detected by a Hall device or the like as engine pulses such as top-dead-center pulses or the like, and the detected engine pulses are supplied to a frequency detecting circuit 11. The frequency detecting circuit 11 generates a base frequency f which is a frequency to be controlled that is a harmonic of the engine rotational speed, and/or a base period Tnep, from the engine pulses.

Specifically, the frequency detecting circuit 11 monitors engine pulses at a frequency much higher than the frequency of the engine pulses to detect times at which the polarity of engine pulses changes, measures time intervals between the polarity changing points to detect the frequency of the engine pulses as the rotational speed of the engine output shaft, and outputs a signal representing a reference frequency f in synchronism with the rotation of the engine output shaft, and/or the base period Tnep which is a control period, based on the detected frequency.

The base frequency f is the reciprocal of the base period Tnep, and is the same as the frequency of the base signal X.

The muffled sound of the engine is a vibrational radiating sound that is generated when vibrational forces produced by the engine rotation are transmitted to the vehicle body. Therefore, the muffled sound of the engine is noise that is highly periodic in synchronism with the engine rotational speed. For example, if the engine is a four-cycle, four-cylinder engine, then it generates vibrations due to torque fluctuations caused when an air-fuel mixture explodes in each one-half of the rotational cycle of the engine output shaft, producing noise in the passenger compartment of the vehicle.

Since the four-cycle, four-cylinder engine generates much noise referred to as a rotational secondary component having a frequency which is twice the frequency of the rotational speed of the engine output shaft, the frequency detecting circuit 11 outputs a signal having a base frequency f (the reciprocal of a base period Tnep) which is twice the detected frequency. The base frequency f is the frequency of the noise to be canceled.

The base period Tnep output from the frequency detecting circuit 11 is input to a sampling period calculating circuit (sampling period calculating means) 12. The sampling period calculating circuit 12 generates sampling pulses (a timing signal) having a sampling period ts for the microcomputer 1, and the microcomputer 1 performs an updating process including a processing sequence such as an LMS algorithm, to be described later, based on the sampling pluses.

Figures 2A, 2B:
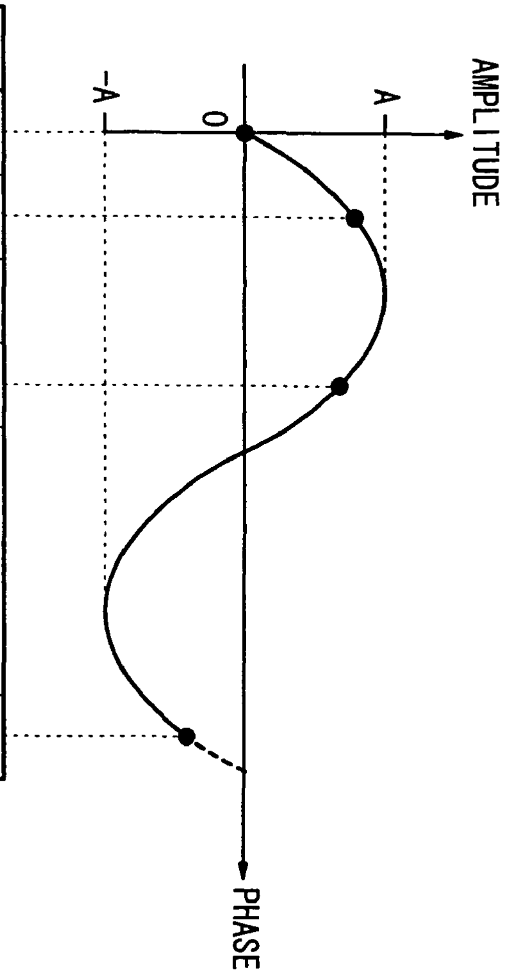
FIG. 2A is a diagram showing waveform data stored in a memory.
FIG. 2B is a diagram showing a sine wave represented by the waveform data stored in the memory.

A waveform data table 19 in the form of a memory stores instantaneous value data as waveform data at respective addresses corresponding to respective phase intervals. As shown in FIGS. 2A and 2B, the instantaneous value data represent instantaneous values produced by dividing a sine wave over one period at equal intervals into a predetermined number (N) of discrete values along the phase axis (time axis). The addresses (i) are represented by integers (i=0, 1, 2, . . . , N−1) ranging from 0 to N−1 (the predetermined number−1). In FIGS. 2A and 2B, an amplitude A represents 1 or a desired positive real number.

The waveform data at an address i is calculated according to A sin(360°×i/N). Stated otherwise, a one-cycle sine wave is sampled (discretized) by being divided into a predetermined number (N) of instantaneous values along the phase axis, i.e., the time axis. Data produced by quantizing the instantaneous values of the sine wave at the respective sampling points are stored as waveform date at respective addresses represented by the sampling points in the waveform data table 19.

In FIG. 1, in response to a signal output from the frequency detecting circuit 11, a first address converting circuit (a first address calculating and specifying means) 20 calculates and specifies addresses based on the base period Tnep (control frequency) as read addresses for the waveform data table 19. A second address converting circuit (a second address calculating and specifying means) 21 calculates and specifies addresses which are shifted by a ¼ period from the addresses specified by the first address converting circuit 20, as read addresses for the waveform data table 19.

The waveform data table 19 corresponds to a storage means for storing waveform data. The frequency detecting circuit 11, the waveform data table 19, the first address converting circuit 20, and the second address converting circuit 21 jointly make up the base signal generating means 22.

Figure 3A:
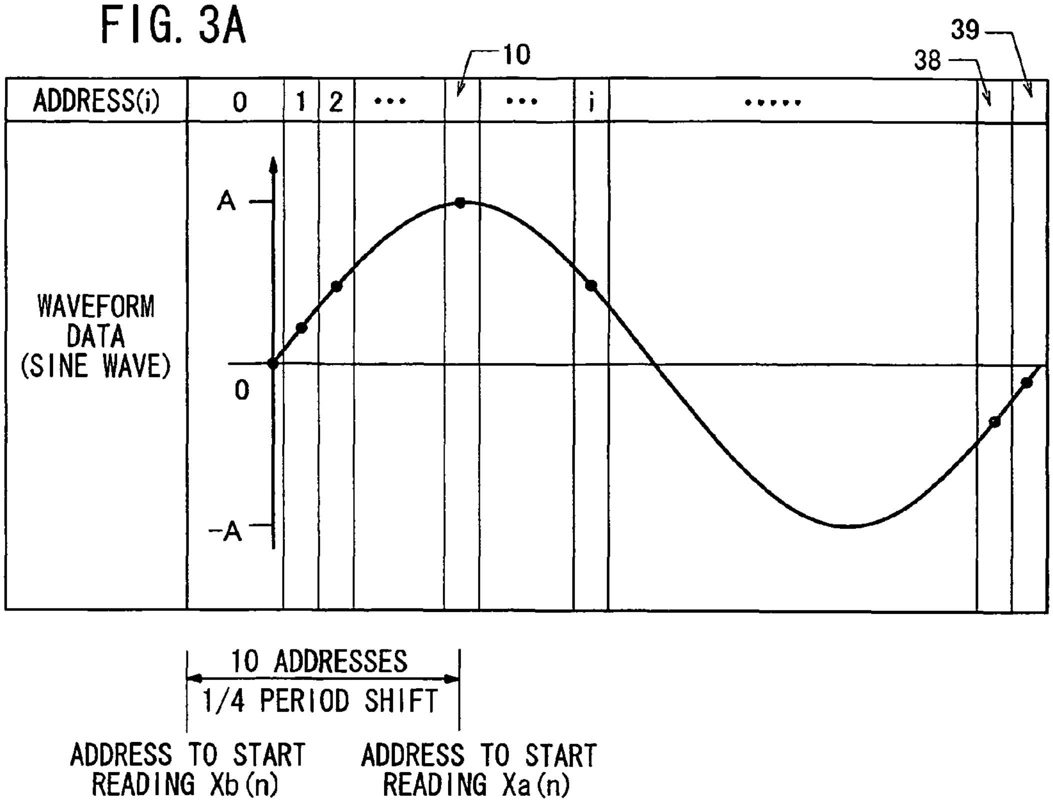
FIG. 3A is a diagram showing waveform data defined by a specific division number.
Figure 3B:
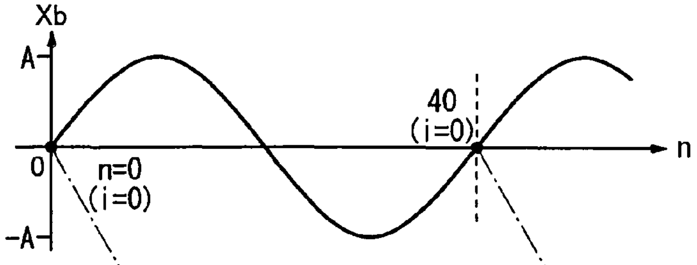
FIG. 3B is a diagram showing a sine wave generated from the waveform data.
Figure 3C:
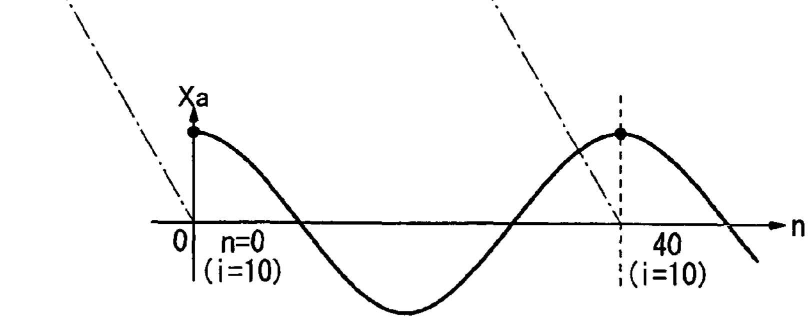
FIG. 3C is a diagram showing a cosine wave generated from the waveform data.

FIGS. 3A through 3C are illustrative of the manner in which the base signal generating means 22 generates a base signal. The manner in which the base signal generating means 22 generates a base signal, i.e., a base cosine-wave signal and a base sine-wave signal, will be described below with reference to FIGS. 3A through 3C.

n represents a positive integer of 0 or greater, and is a count of the sampling pulses (timing signal count). FIG. 3A schematically shows the relationship between the addresses of the waveform data table 19 and the waveform data. FIG. 3B schematically shows how to generate the base sine-wave signal Xb, and FIG. 3C schematically shows how to generate the base cosine-wave signal Xa.

For an easier understanding of the active vibration noise control apparatus 10, the conventional variable sampling technology (synchronous sampling technology) will first be described in specific detail below.

The frequency detecting circuit 11 outputs sampling pulses at a sampling period in synchronism with the rotational speed of the engine output shaft (engine rotational speed). The predetermined number (N) is assumed to be 40. Therefore, the addresses are i=0, 1, 2, . . . , N−1=0, 1, 2, . . . , 39. The ¼-period address shift is N/4=10.

According the synchronous sampling technology, the sampling interval changes depending on (in synchronism with) the engine rotational speed. The sampling period calculating circuit 12 outputs sampling pulses at a sampling period (interval, time) ts based on the equation (1) shown below, depending on the base frequency f output from the frequency detecting circuit 11.

$$ts=Tnep/N=1/(f \times N)=1/(f \times 40)[\text{sec.}] \quad (1)$$

The first address converting circuit 20 increments the address by 1, as indicated by the equation shown below, for each sampling pulse output from the sampling period calculating circuit 12, thereby specifying read addresses; i(n). The address i(n) at a certain time is expressed by:

$$i(n)=i(n-1)+1$$

If $i(n)>39(=N-1)$, then $$i(n)=i(n-1)+1-40$$

Therefore, the base signal generating means 22 generates a base sine-wave signal Xb(n) by successively reading the waveform data from the waveform data table 19 while incrementing the address by 1 for each sampling pulse output from the sampling period calculating circuit 12. For example, if the control frequency is 20 Hz, then when the control process is started, the base signal generating means 22 generates a base sine-wave signal Xb(n) of 20 Hz by successively reading the waveform data from the addresses i(n)=0, 1, 2, 3, . . . , 39, 0, . . . of the waveform data table 19 for respective sampling pulses generated at intervals 1/800 [sec.]. If the control frequency is 25 Hz, then when the control process is started, the base signal generating means 22 generates a base sine-wave signal Xb(n) of 25 Hz by successively reading the waveform data from the addresses i(n)=0, 1, 2, 3, . . . , 39, 0, . . . of the waveform data table 19 for respective sampling pulses generated at intervals 1/1000 [sec.].

The second address converting circuit 21 specifies addresses produced by shifting (incrementing), by a ¼ period, the read addresses i(n) specified by (output from) the first address converting circuit 20 for generating the base sine-wave signal Xb(n), as read addresses i'(n), according to the following equation:

$$i'(n)=i(n)+N/4=i(n)+10$$

If $i'(n)>39(=N-1)$, then $$i'(n)=i(n)+10-40$$

Therefore, the base signal generating means 22 generates a base cosine-wave signal Xa(n) by successively reading the waveform data from the addresses, shifted in phase by a ¼ period from the read starting addresses, of the waveform data table 19 at an address interval corresponding to the control frequency, for each sampling pulse generated by the sampling period calculating circuit 12.

For example, if the control frequency is 20 Hz, then when the control process is started, the base signal generating means 22 generates a base cosine-wave signal Xa(n) of 20 Hz by successively reading the waveform data from the addresses i'(n)=10, 11, 12, 13, . . . , 9, 10, . . . of the waveform data table 19 for respective sampling pulses generated at intervals 1/800 [sec.]. If the control frequency is 25 Hz, then when the control process is started, the base signal generating means 22 generates a base cosine-wave signal Xa(n) of 25 Hz by successively reading the waveform data from the addresses i'(n)=10, 11, 12, 13, . . . , 9, 10, . . . of the waveform data table 19 for respective sampling pulses generated at intervals 1/1000 [sec.].

According to the synchronous sampling technology, therefore, the base signal X is generated by changing time intervals for reading the waveform data depending on the control frequency.

In this manner, the base signal X which comprises the base sine-wave signal Xb and the base cosine-wave signal Xa depending on the harmonic of the base period Tnep is generated.

In the above example, instantaneous values produced by dividing a sine waveform over one period into a predetermined number (N) of values along the time axis (phase axis) are stored in the waveform data table 19. However, instantaneous values produced by dividing a cosine waveform over one period into a predetermined number (N) of values along the time axis (phase axis) may be stored in the waveform data table 19.

In the latter case, read addresses; i(n) for the base sine-wave signal are specified as addresses that are shifted by a ¼ period according to $\cos(\theta-\pi/2)=\sin(\theta)$ from the read addresses i'(n) for the base cosine-wave signal.

The base cosine-wave signal Xa and the base sine-wave signal Xb thus generated make up the base signal X having a harmonic frequency (base period Tnep) of the frequency of the rotational speed of the engine output shaft, and have the frequency of the noise to be canceled.

As shown in FIG. 1, the base cosine-wave signal Xa is supplied to a first adaptive notch filter 14*a*. The first adaptive notch filter 14*a* has filter coefficients adaptively processed and updated for each sampling pulse by a filter coefficient updating means 30*a* such as an LMS algorithm unit (an LMS algorithm processing means) or the like. The base sine-wave signal Xb is supplied to a second adaptive notch filter 14*b*. The second adaptive notch filter 14*b* has filter coefficients adaptively processed and updated for each sampling pulse by a filter coefficient updating means 30*b* such as an LMS algorithm unit (an LMS algorithm processing means) or the like.

An output signal (a first control signal ya) from the first adaptive notch filter 14*a* and an output signal (a second control signal yb) from the second adaptive notch filter 14*b* are supplied to an adder 16, which adds the first control signal ya and the second control signal yb into a control signal y. The control signal y is converted by a D/A converter 17*a* into an analog signal, which is supplied through a low-pass filter (LPF) 17*b* and an amplifier (AMP) 17*c* to the speaker 17, which radiates a corresponding sound.

Specifically, the sum output signal (noise canceling signal) from the adder 16 is supplied as the control signal y to the speaker 17 disposed in the passenger compartment for generating canceling noise. Therefore, the speaker 17 is driven by the control signal y output from the adder 16. The microphone 18 is also disposed in the passenger compartment for detecting residual noise in the passenger compartment and outputting the detected residual noise as a residual noise signal (error signal) e.

A signal output from the microphone 18 is supplied through an amplifier (AMP) 18*a* and a bandpass filter (BPF) 18*b* to an A/D converter 18*c*. The A/D converter 18*c* converts the signal into a digital signal, which is supplied as the residual noise signal e to the filter coefficient updating means 30*a*, 30*b*.

The active vibration noise control apparatus 10 also has a memory 23 serving as a corrective data storage means for storing, with respect to control frequencies, address shift values which serve as corrective values based on a phase delay in the signal transfer characteristics between the speaker 17 and the microphone 18 with respect to each control frequency, i.e., address shift values for the addresses of the waveform data table 19, an adding circuit 25 for adding an address shift value read from an address of the memory 23 which is specified based on the control frequency depending on the output signal from the frequency detecting circuit 11, to address data output from the first address converting circuit 20, and specifying an address of the waveform data table 19 based on the sum value, an adding circuit 24 for adding the address shift value read from the memory 23 to address data output from the second address converting circuit 21, and specifying an address of the waveform data table 19 based on the sum value, and gain setting units 26, 27 for setting a gain magnification serving as a corrective value based on a gain change in the signal transfer characteristics between the speaker 17 and the microphone 18 with respect to each control frequency, for waveform data read from the addresses of the waveform data table 19 which have been specified by output signals from the adding circuits 24, 25.

The memory 23, the adding circuits 24, 25, and the gain setting units 26, 27 jointly make up the reference signal generating means 28 for generating a reference signal r from the base signal X. A control frequency is referred to, and an address shift value depending on the control frequency, or stated otherwise the base period Tnep, is read from the memory 23. The address shift value is added to the address data output from the second address converting circuit 21, and waveform data is read from an address of the waveform data table 19 based on the sum value. The read waveform data is then multiplied by the gain magnification by the gain setting unit 26, which outputs a first reference signal rx.

The address shift value is also added to the address data output from the first address converting circuit 20, and waveform data is read from an address of the waveform data table 19 based on the sum value. The read waveform data is then multiplied by the gain magnification by the gain setting unit 27, which outputs a second reference signal ry.

The first reference signal rx is a signal based on the base cosine-wave signal Xa of the control frequency which is shifted in phase by a value based on the address shift value, and the second reference signal ry is a signal based on the base sine-wave signal Xb of the control frequency which is shifted in phase by a value based on the address shift value.

The first reference signal rx output from the gain setting unit 26 and the residual noise signal e output from the microphone 18 are supplied to the filter coefficient updating means 30*a*, which processes the supplied signals according to an LMS algorithm. Based on an output signal from the filter coefficient updating means 30*a*, the filter coefficients of the first adaptive notch filter 14*a* are updated for each sampling pulse (sampling period) in order to minimize the output signal from the microphone 18, i.e., the residual noise signal e. The second reference signal ry output from the gain setting unit 27 and the residual noise signal e output from the microphone 18 are supplied to the filter coefficient updating means 30*b*, which processes the supplied signals according to an LMS algorithm. Based on an output signal from the filter coefficient updating means 30*b*, the filter coefficients of the second adaptive notch filter 14*b* are updated for each sampling pulse (sampling period) in order to minimize the output signal from the microphone 18, i.e., the residual noise signal e.

Figure 17:
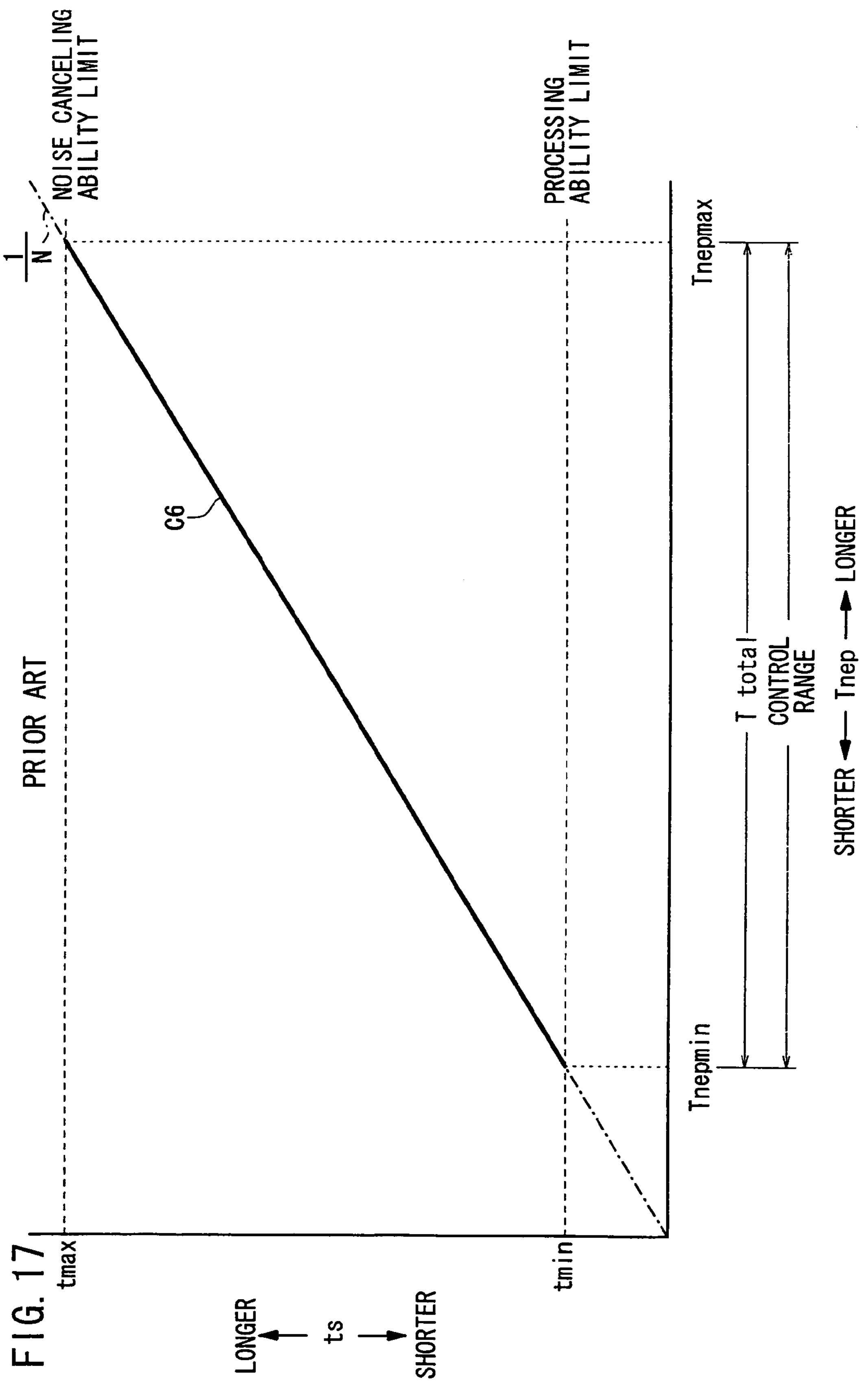
FIG. 17 is a diagram illustrative of limits on a control range according to the conventional variable sampling technology (synchronous sampling technology).

According to the synchronous sampling technology, as described above with reference to FIG. 17, if a division number n is determined, then the sampling period ts can be determined as ts=Tnep/N from the base period Tnep. Because as the base period Tnep is smaller, the sampling period ts is shorter, there is a trade-off problem between the processing ability limit (=shortest sampling period=processing ability limit sampling period) of the CPU of the microcomputer or the like and the control range. Specifically, if the control range is to be widened into a higher frequency range on a shorter base period Tnep, then a need arises for a microcomputer having a fast high-performance CPU with a high processing ability limit as shown in FIG. 17.

An active vibration noise control apparatus 2 based on the variable sampling technology, which allows a control range to be designed with greater freedom and poses less strict limits on the processing ability of a CPU for achieving a wider control range, will be described below.

The above active vibration noise control apparatus 2 is capable of performing a control process for a smooth noise canceling capability, i.e., an effective noise canceling control process, even when the base period of the base signal that is generated depending on the vibrational noise of the noise source contains fluctuations.

1st Embodiment

The number of updates in one period of the base signal X is set to a division number m=m1.

According to the first embodiment, the division number m1 is determined by dividing a first upper limit base period TU1 of a control range Tca1 shown in FIG. 4 by the noise canceling ability limit sampling period tmax according to the equation (2) shown below. The control range Tca1 refers to a predetermined range (particular range) within a control range Ttotal.

$$m1=TU1/t\max \tag{2}$$

where the division number m1 is a positive real number. According to the conventional sampling technology, the division number N is a natural number.

The first upper limit base period TU1 may not be a longest period in the control range, but may be set to a shorter particular base period.

Then, a first identical division number lower limit base period TL1 which is a shorter period in the control range Tca1 of the base period Tnep is determined by multiplying the division number m1 determined according to the equation (2) by the processing ability limit period tmin of the CPU, according to the following equation (3):

$$TL1=m1\times t\min \tag{3}$$

The freedom of design can be increased by thus determining the division number m1 to be a real number.

Inasmuch as noise having a base frequency f (the reciprocal of the control period Tnep) corresponding to the first upper limit base period TU1 in a certain control range Tca1 is updated at the noise canceling ability limit sampling period tmax, the noise canceling capability for the noise is guaranteed. The noise is reliably canceled because the lower limit base period TL1 is not smaller than the processing ability limit period tmin.

Figure 4:
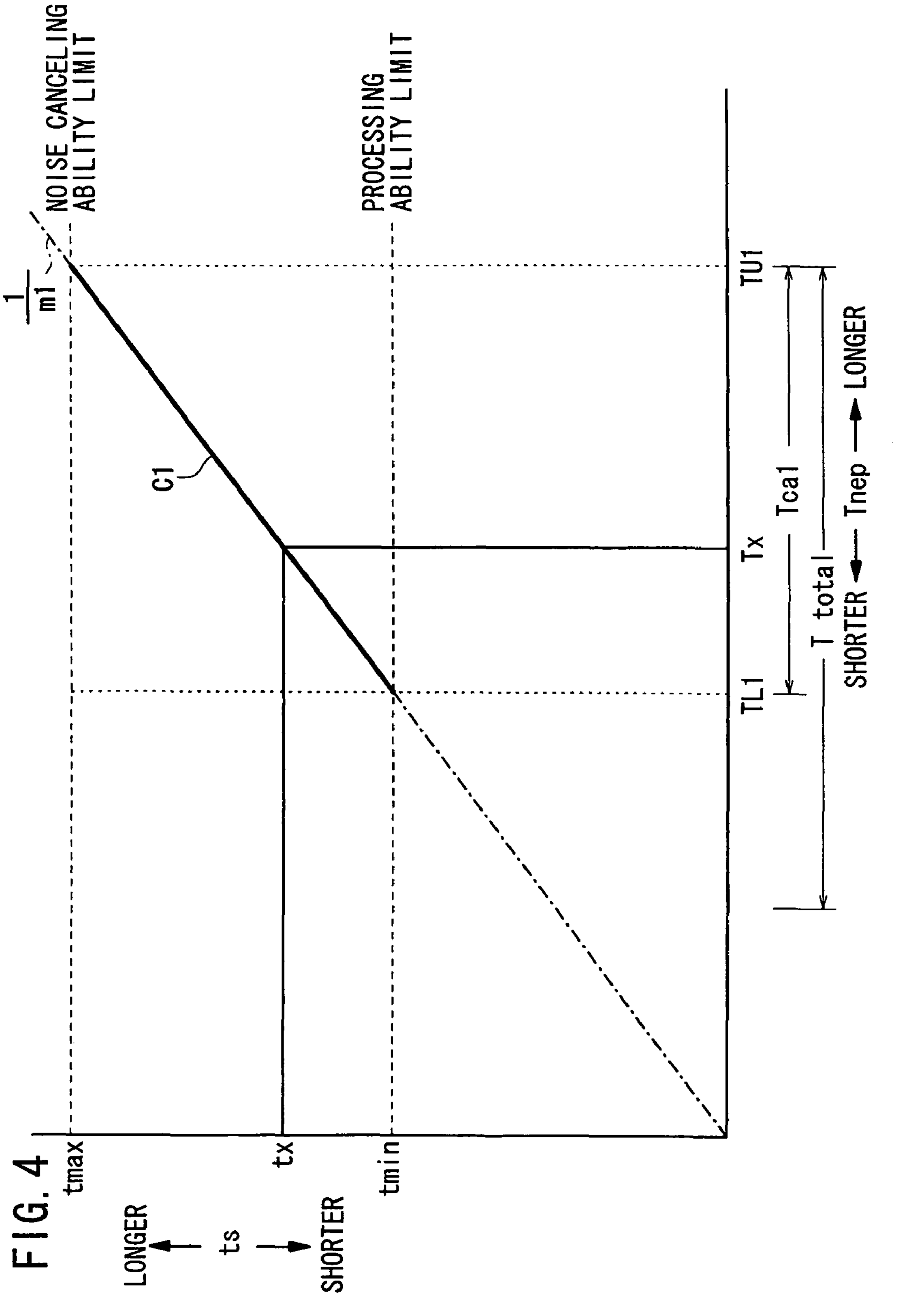
FIG. 4 is a diagram illustrative of a process of calculating a sampling period according to a first embodiment of the present invention.

According to the first embodiment, in a certain control range Tca1, the sampling period ts corresponding to the base period Tnep is determined according to a sampling period curve C1 (C1=1/m1) indicated by the thick solid line in FIG. 4.

For example, it is assumed that the base period Tnep is detected from engine pulses by the frequency detecting circuit 11 as the base period Tnep=Tx as shown in FIG. 4.

At this time, the sampling period (the period of sampling pulses) ts=tx output from the sampling period calculating circuit 12 is determined from the detected base period Tx and the division number m1 determined by the equation (2), according to the following equation (4):

$$tx=Tx/m1 \quad (4)$$

Since the division number m1 is determined to be a real number unlike the predetermined number N in the equation (1), it is necessary to rely on a certain approach to read waveform data from the waveform data table 19 as described below.

The first address converting circuit 20 calculates a step number (address step number) P for each sampling period ts, i.e., for the arrival of each sampling pulse. The step number P is determined as follows:

The division number m1 is of a value produced by dividing the upper limit base period TU1 in a certain control range Tca1 by the noise canceling ability limit sampling period tmax for achieving a noise canceling capability. Stated otherwise, the division number m1 corresponds to the number of updates (=the number of calculations=the number of filter coefficient updates=the number of noise canceling processes) in one period of the base signal X whose base frequency corresponds to the upper limit base period TU1.

Since the sampling period tx in the certain control range Tca1 is indicated by the equation (4), the division number m1 represents the number of updates in one period of the base signal X whose base frequency is included in the certain control range Tca1.

Therefore, in order to make m1 updates in one period of the base signal X, the waveform data have to be read at certain intervals (step number P) in each sampling period.

The value of an integer (=quotient) of a value produced when the predetermined number N representing the total number of waveform data is divided by the division number m1 determined by the equation (2), or a value (=quotient+1) produced when the decimal part of the produced value is rounded up, is used as the step number P. The step number P is thus the same as either the quotient produced when the predetermined number N is divided by the division number m1 or a number produced when 1 is added to the quotient.

When the base period Tnep is present in the control range Tca1 between the first upper limit base period TU1 and the identical division number lower limit base period TL1, waveform data are read from the waveform data table 19 for each step number P in the sampling period ts (ts=Tnep/m1) depending on a value produced when the detected base period Tnep is divided by the division number m1, for thereby generating the base signal X (the base cosine-wave signal Xa and the base sine-wave signal Xb). The first and second reference signals rx, ry are generated from the base signal X.

Figure 5:
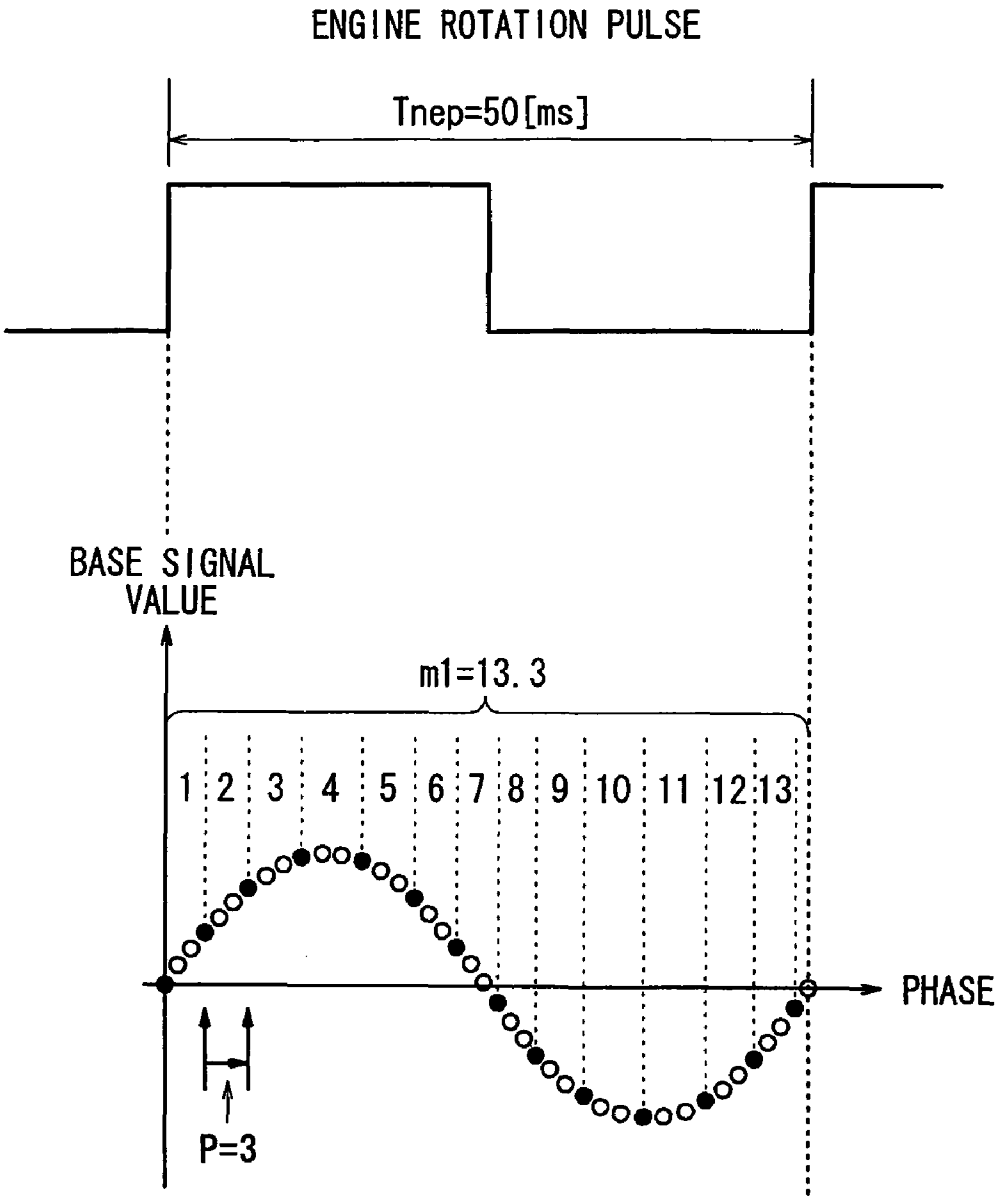
FIG. 5 is a diagram illustrative of the manner in which waveform data are read at each predetermined step number in the sampling period calculated based on the characteristic curve shown in FIG. 4 and a base signal is generated.

Specifically, as shown in FIG. 5, when the base period Tnep is Tnep=50 [ms] and the division number m1 is m1=13.3, since the division N/m1=40/13.3 produces a quotient of 3 and a remainder of 0.1, the step number P is calculated as P=3 with the decimal part being rounded down.

At this time, the waveform data "0, A sin(360°×3/40), A sin(360°×6/40), . . . , A sin(360°×39/40)" which are indicated by the solid dots at the addresses "0, 3, 6, . . . , 36, 39" are read from the waveform data table 19, generating the base sine-wave signal Xb. If the base period Tnep is free of fluctuations, then in order to keep the waveform continuous, waveform data for generating a base signal X next to the addresses "0, 3, 6, . . . , 36, 39" may be read from addresses "2, 5, 8, . . . , 35, 38" in view of the step number P=3.

According to the first embodiment, as described above, the active vibration noise control apparatus 10 has the speaker 17 as a control sound source for radiating a control sound into a space through which noise is transmitted from the noise source such as an engine or the like, the frequency detecting circuit 11 as a frequency detecting means for detecting a noise generating state of the noise source and outputting a harmonic base frequency selected from the frequencies of the noise generated from the noise source and a base period Tnep corresponding to the base frequency, the microphone 18 as a residual noise detecting means for detecting residual noise at a predetermined position in the space, and the active control means 32 for driving the speaker 17 to reduce the noise in the space based on a base signal X (Xa, Xb) and the residual noise.

The active control means 32 has the waveform data table 19 for storing sine or cosine waveform data discretized into the predetermined number N of values, the sampling period calculating circuit 12 as a sampling period calculating means for calculating a sampling period ts based on the base period Tnep, and the base signal generating means 22 for reading waveform data from the waveform data table 19 and generating the base signal X (Xa, Xb).

The sampling period calculating circuit 12 uses the base period Tnep of a particular base signal in the control range Ttotal as the upper limit base period TU1, determines the division number m1 which is of a value produced when the upper limit base period TU1 is divided by the upper limit sampling period tmax required for the active control means 32 to obtain a noise canceling capability, and uses a period produced when the lower limit sampling period tmin which is a limit of the processing ability of the active control means 32 is multiplied by the division number m1, as the identical division number lower limit base period TL1.

If the base period of the base signal X is present between the upper limit base period TU1 and the identical division number lower limit base period TL1, then a value produced when the base period Tx of the base signal X is divided by the division number m1 is output as the sampling period tx.

The base signal generating means 22 uses the quotient produced when the predetermined number N is divided by the division number m1 or a value produced when 1 is added to the quotient, as a step number P1, and reads waveform data from the waveform data table 19 for each step number P1 in the sampling period tx to generate the base signal X.

According to the first embodiment, since the step number P for reading discrete waveform data is the quotient produced when the predetermined number N representing the total number of waveform data is divided by the division number m1 or a value represented by the quotient+1, the division number m1 used in the variable sampling technology is not limited to only a natural number as with the prior art, but may be a real number, allowing the control range to be designed with increased freedom. Stated otherwise, using a real number as the division number m1 makes it possible to set the noise canceling ability limit sampling period tmax or the processing ability limit sampling period tmin to the sampling period ts as a requisite minimum.

The upper limit base period TU1 as the base period Tnep of the particular base signal may be a longest base period in the control range Tca1 or a shorter base period.

2nd Embodiment

A process according to a second embodiment, which is performed when the detected base period Tnep is shorter than the first identical division number lower limit base period TL1 at the lower limit of the control range Tca1 (the engine rotational speed is higher), as shown in FIG. 4, will be described below. According to the second embodiment, a wider control range Ttotal can be controlled by the same CPU, i.e., a CPU having the same processing ability limit, or in other words, without making the processing ability limit sampling period tmin shorter.

For an easier understanding of the second embodiment, the identical division number lower limit base period TL1 shown in FIG. 4 is also referred to as a second upper limit base period TU2.

In the second embodiment, a value produced when the second upper limit base period TU2 is divided by the noise canceling ability limit sampling period tmax is used as a second division number m2 (real number), as with the equation (2).

Figure 6:
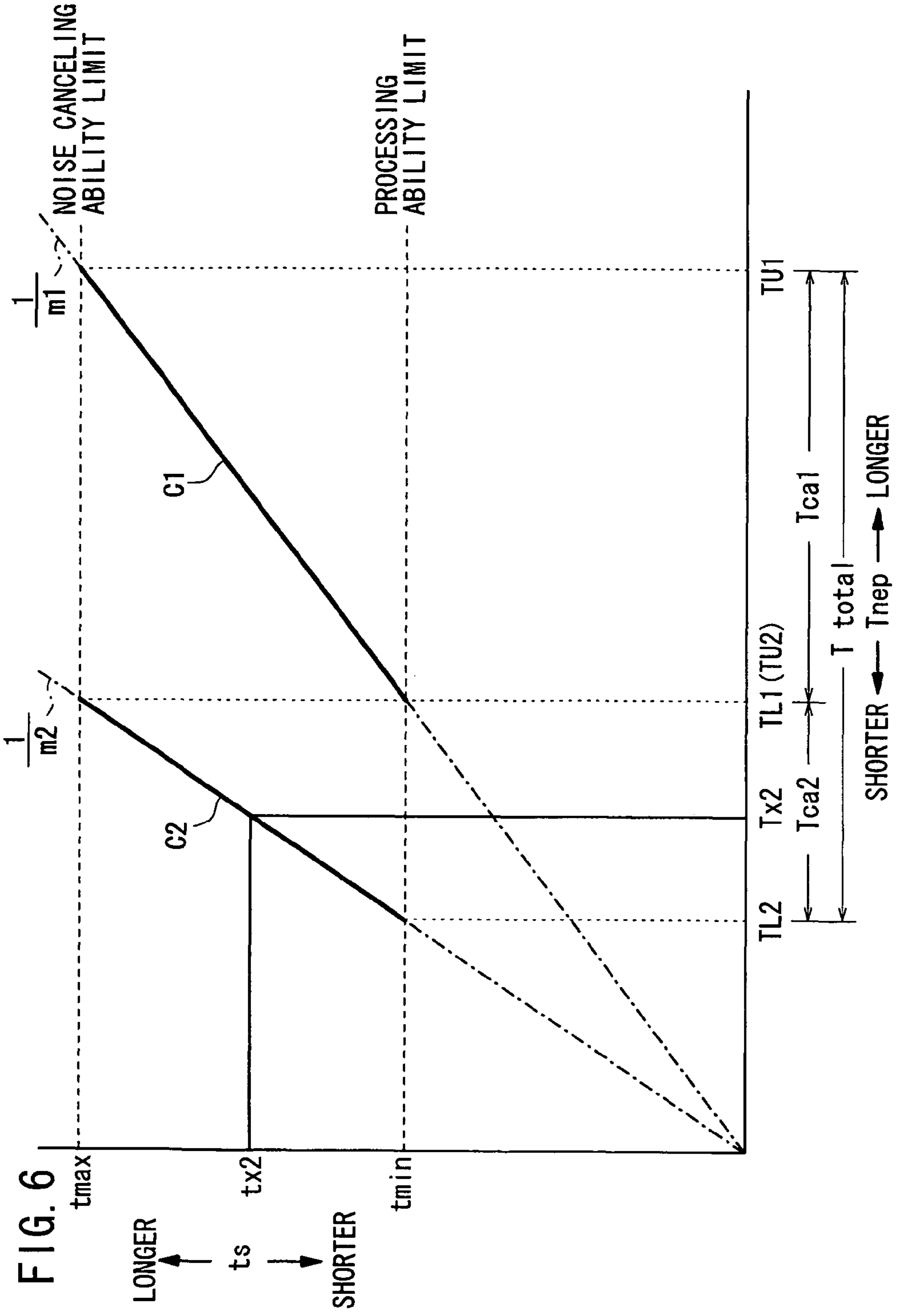
FIG. 6 is a diagram illustrative of a process of calculating a sampling period according to a second embodiment of the present invention in which a control range is widened without changing the processing ability limit to a shorter sampling period.

As shown in FIG. 6, a second identical division number lower limit base period TL2 is determined as TL2=m2×tmin as with the equation (3).

In the second embodiment, a sampling period ts=tx2 corresponding to a base period Tnep=Tx2 shorter than the second upper limit base period TU2 included in a second control range Tca2 is determined as tx2=Tx2/m2 as with the equation (4), based on a sampling period characteristic curve C2 indicated by the thick solid line in FIG. 6.

In the second embodiment, if the control range is greater than the range determined by the upper limit base period TU1 and the identical division number lower limit base period TL1, then the sampling period calculating circuit 12 uses the identical division number lower limit base period TL1 as the second upper limit base period TU2, determines the second division number m2 having a value which is produced when the second upper limit base period TU2 is divided by the upper limit sampling period tmax, uses a period produced when the lower limit sampling period tmin is multiplied by the second division number m2 as the second identical division number lower limit base period TL2, outputs a value produced when the base period Tnep is divided by the second division number m2 as the second sampling period tx2 if the base period Tnep is the base period Tx2 within the range between the second upper limit base period TU2 and the second identical division number lower limit base period TL2.

The base signal generating means 22 uses the quotient produced when the predetermined number N is divided by the second division number m2 or a value produced when 1 is added to the quotient, as a second step number P2, and reads waveform data from the waveform data table 19 for each second step number P2 in the second sampling period tx2 to generate the base signal X if the base period Tnep is within the second range between the second upper limit base period TU2 and the second identical division number lower limit base period TL2.

According to the second embodiment, the control range for the base period Tnep can be set to a wide control range Ttotal which is a combination of the control range Tca1 and the control range Tca2, without changing the processing ability limit sampling period tmin corresponding to the processing ability limit of the CPU.

As described above, the step number P on the sampling period characteristic curve C2 is set to the quotient produced when the predetermined number N representing the total number of waveform data is dividable by the second division number m2 or the quotient+1.

Thus, when the base period Tnep is present in the control range Tca2 between the second upper limit base period TU2 and the second identical division number lower limit base period TL2, waveform data are read from the waveform data table 19 for each step number P (the quotient produced when the predetermined number N is divided by the division number m2 or the quotient+1) in the sampling period ts (ts=Tnep/m2) depending on a value produced when the detected base period Tnep is divided by the division number m2, for thereby generating the base signal X (the base cosine-wave signal Xa and the base sine-wave signal Xb), and the first and second reference signals rx, ry.

Figure 7:
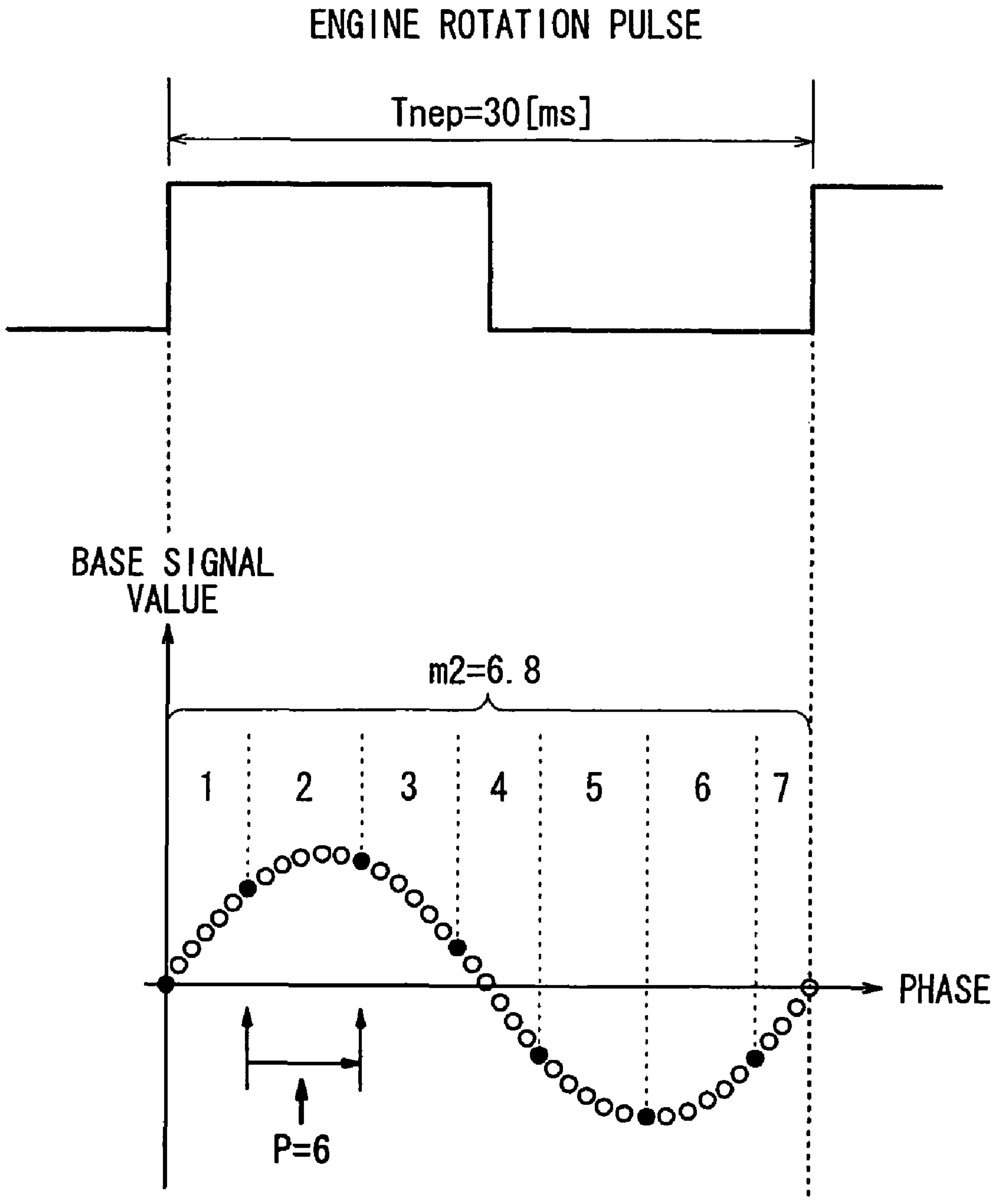
FIG. 7 is a diagram illustrative of the manner in which waveform data are read at each predetermined step number in the sampling period calculated based on the characteristic curve shown in FIG. 6 and a base signal is generated.

Specifically, as shown in FIG. 7, when the base period Tnep is Tnep=30 [ms] and the division number m2 is m2=6.8, since the division N/m2=40/6.8 produces a quotient of 5 and a decimal part of 0.882 . . . , the step number P is calculated as P=6 (the quotient+1) with the decimal part being rounded up.

At this time, the waveform data "0, $A\sin(360°\times 6/40)$, $A\sin(360°\times 12/40)$, . . . , $A\sin(360°\times 36/40)$" which are indicated by the solid dots at the addresses "0, 6, 12, . . . , 30, 36" are read from the waveform data table 19. If the base period Tnep is free of fluctuations, then in order to keep the waveform continuous, waveform data for generating a next base signal X may be read from addresses "2, 8, 14, . . . , 32, 38" in view of the step number P=6.

3rd Embodiment

Actually, the engine rotational speed in a cruise control mode (constant speed control) suffers fluctuations of ±10 [rpm] due to air-fuel combustion fluctuations in the engine when the engine rotational speed is 2000 [rpm], for example. When the engine operates not in the cruise control mode, the engine rotational speed tends to fluctuate because of an unconscious small action made by the user on the accelerator pedal for driving the vehicle at a constant speed.

Therefore, if the detected base period Tnep is of a value close to the second upper limit base period TU2 in FIG. 6, then switching occurs between the sampling period characteristic curve C1 and the sampling period characteristic curve C2. Since the division number m switches between the division number m1 and the division number m2, the number of updates in the active control varies, making the active control unstable. Consequently, the noise canceling capability is liable to vary slightly.

According to the third embodiment, the limits on the processing ability of the CPU are made much less strict to provide a wider control range, and even when the base period Tnep fluctuates, a control process for a smooth noise canceling capability, i.e., an effective noise canceling control process, is performed.

Figure 8:
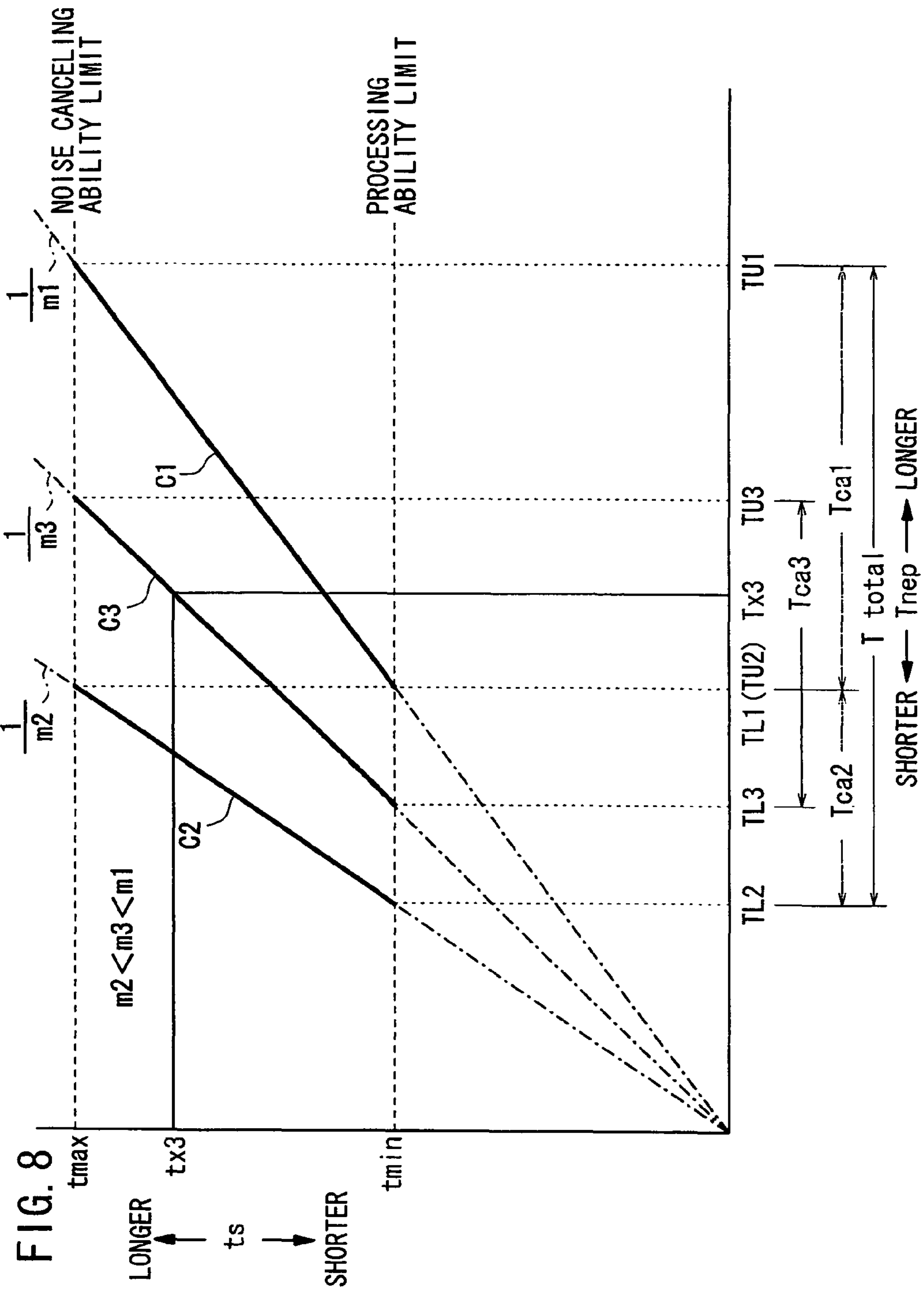
FIG. 8 is a diagram illustrative of a smoother updating control process according to a third embodiment of the present invention, within the control range according to the second embodiment.

As shown in FIG. 8, the base signal generating means 22 uses a particular period between the first upper limit base period TU1 and the second upper limit base period TU2 as a third upper limit base period TU3.

A value produced when the third upper limit base period TU3 is divided by the noise canceling ability limit sampling period tmax is used as a third division number m3 (real number), as with the equation (2).

A value produced when the third division number m3 is multiplied by the CPU processing ability limit sampling period tmin is used as a third identical division number lower limit base period TL3 (TL3=m3×tmin) in the control range Ttotal, as with the equation (3).

In the third embodiment, a sampling period ts=tx3 corresponding to a base period Tnep=Tx3 included in a third control range Tca3 is determined as tx3=Tx3/m3 as with the equation (4), based on a sampling period characteristic curve C3 indicated by the thick solid line in FIG. 8.

The step number P on the sampling period characteristic curve C3 is set to the quotient produced when the predetermined number N representing the total number of waveform data is dividable by the third division number m3 or the quotient+1.

Figure 9:
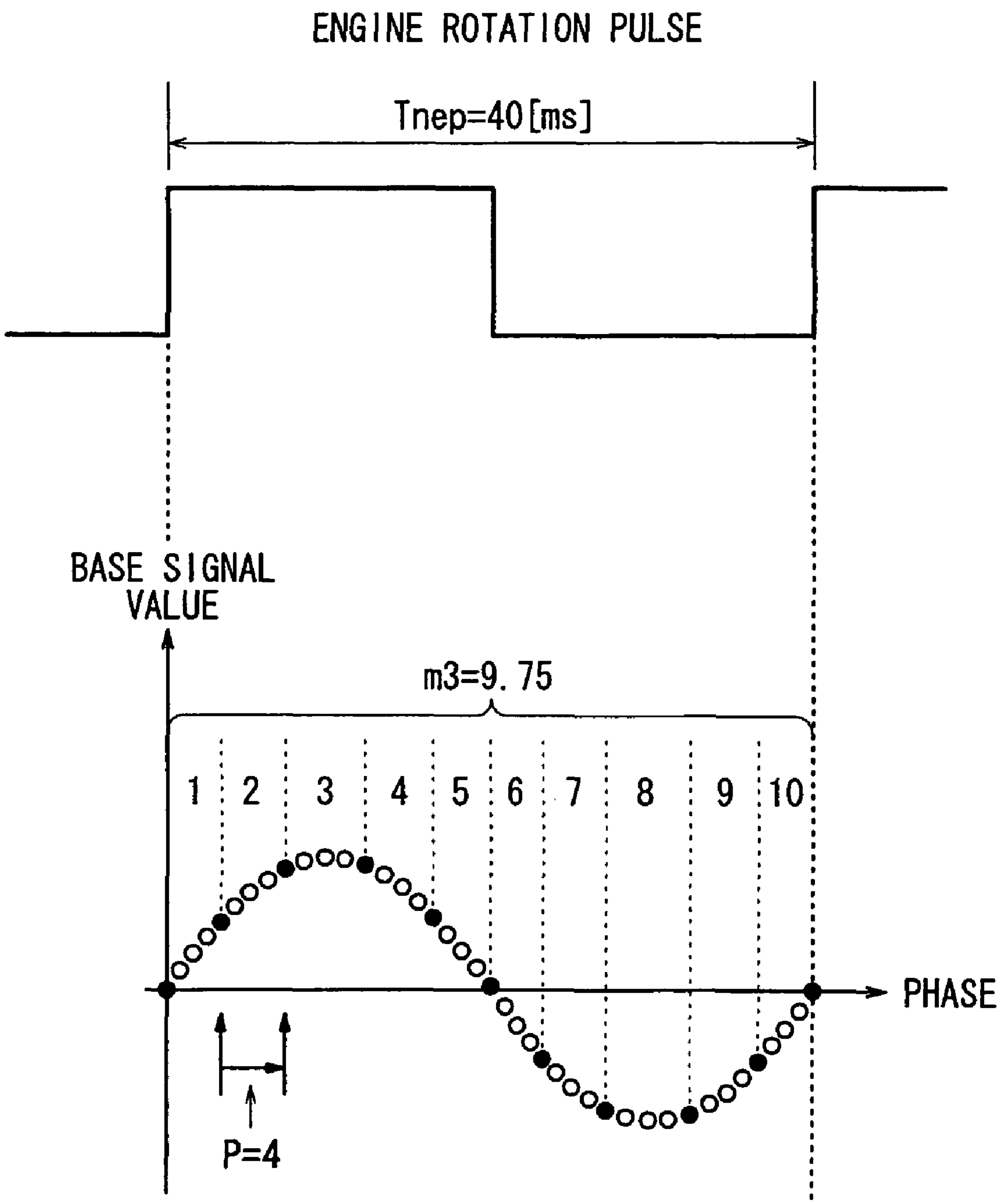
FIG. 9 is a diagram illustrative of the manner in which waveform data are read at each predetermined step number in the sampling period calculated based on the characteristic curve shown in FIG. 8 and a base signal is generated.

Specifically, as shown in FIG. 9, when the base period Tnep is Tnep=40 [ms] and the division number m3 is m3=9.75, since the division N/m3=40/9.75 produces a quotient of 4 and a decimal part of 0.102 . . . , the step number P is calculated as P=4 (which is equal to the quotient of N/m3=40/9.75) with the decimal part being rounded down.

At this time, the waveform data "0, $A\sin(360°\times 4/40)$, $A\sin(360°\times 8/40)$, . . . , $A\sin(360°\times 36/40)$" which are indicated by the solid dots at the addresses "0, 4, 8, . . . , 32, 36" are read from the waveform data table 19. If the base period Tnep is free of fluctuations, then in order to keep the waveform continuous, waveform data for generating a next base signal X may be read from addresses "0, 4, 8, . . . , 32, 36" in view of the step number P=4.

Figure 10:
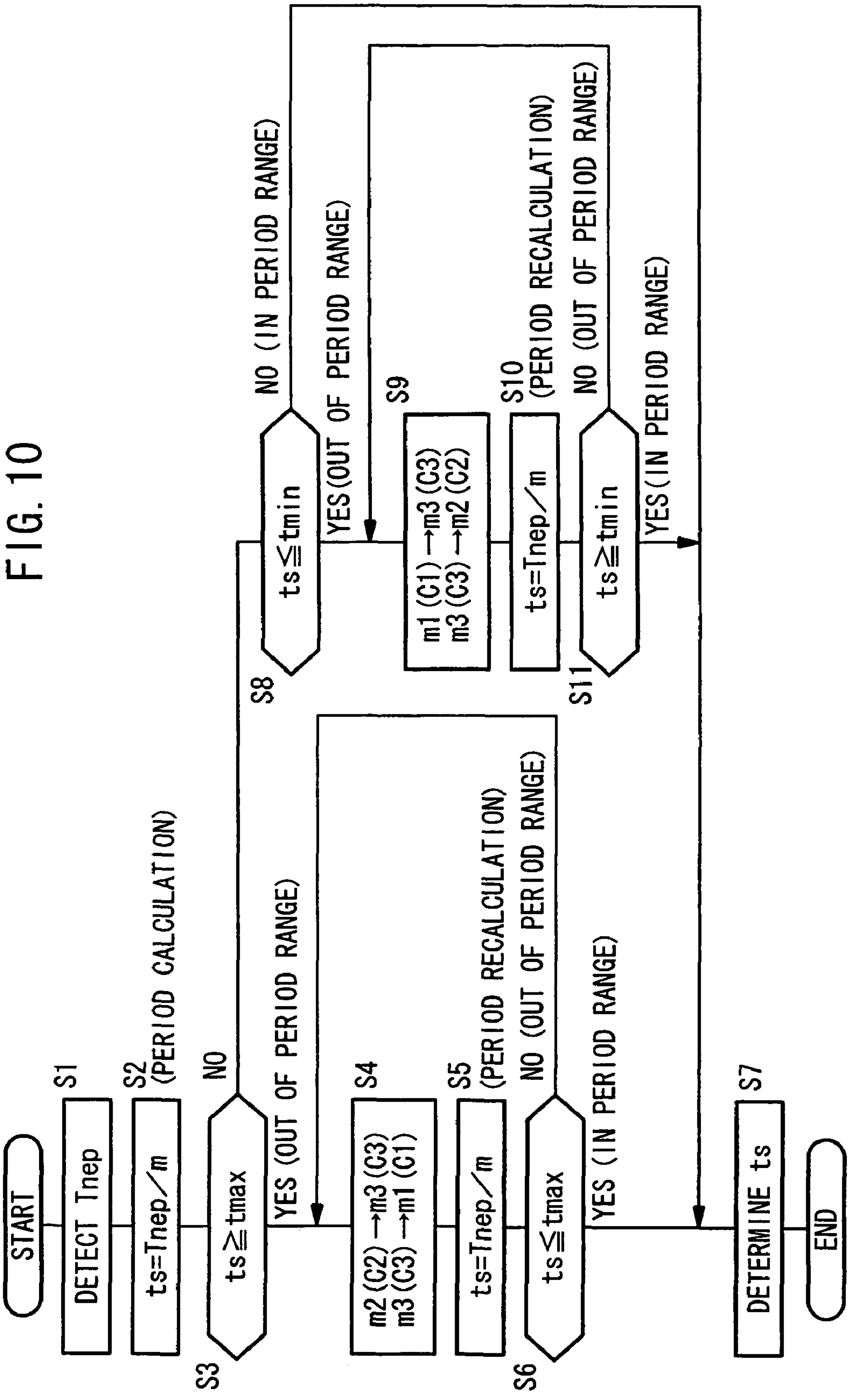
FIG. 10 is a flowchart of an operation sequence according to the third embodiment.

A control process for updating filter coefficients based on a so-called hysteresis control process, using the sampling period characteristic curves C1, C2, C3 shown in FIG. 8 will be described below with reference to a flowchart shown in FIG. 10. The flowchart represents a program executed by the microcomputer 1 (the base signal generating means 22) for determining the sampling period ts.

In step S1, the frequency detecting circuit 11 detects a present base period Tnep. In step S2, a sampling period ts (ts=Tnep/m) to be used in a present control cycle is determined according to the equation (4) based on the detected base period Tnep, by referring to the sampling period characteristic curve C (either one of the curves C1 through C3) or the division number m (either one of the division numbers m1 through m3) used to calculate the sampling period ts in the preceding control cycle. At the start of the control process, the division number m is set to m=m1.

For an easier understanding of the control process, it is assumed that the sampling period characteristic curve C used in the preceding control cycle is the sampling period characteristic curve C3 (the division number m3).

In step S3, the sampling period ts to be used in the present control cycle which is calculated in step S2 and the noise canceling ability limit sampling period tmax are compared with each other to determine whether or not the sampling period ts is greater than or equal to the noise canceling ability limit sampling period tmax (ts≧tmax ?).

If the vehicle is decelerating, i.e., if the base period Tnep is increasing in the control range according to the sampling period characteristic curve C3 (the range from the third identical division number lower limit base period TL3 to the third upper limit base period TU3), and the presently detected base period Tnep is of a value greater than the third upper limit base period TU3 as compared with the time when the sampling period ts was calculated in the preceding control cycle, then since the sampling period ts exceeds the range of the sampling period characteristic curve C3, the determination in step S3 becomes affirmative. In step S4, the division number m is then changed to change the sampling period characteristic curve C to a characteristic curve closer to the upper limit base period.

Inasmuch as the base period Tnep is of a value greater than the third upper limit base period TU3, the division number m changes from the division number m3 to the division number m1, so that the sampling period characteristic curve C3 changes to the sampling period characteristic curve C1.

If the preceding base period Tnep is of a value smaller than the second upper limit base period TU2 and the present base period Tnep is of a value greater than the second upper limit base period TU2, then the division number m changes from the division number m2 to the division number m3, and the sampling period characteristic curve C2 changes to the sampling period characteristic curve C3.

In step S5, the sampling period ts (ts=Tnep/m1) to be used in the present control cycle is calculated again with the changed division number m1.

By thus calculating the sampling period ts while the division number m is changing from the division number m3 to the division number m1, since the division numbers m1 through m3 are related to each other according to m2<m3<m1 as shown in FIG. 8, if the sampling period ts becomes shorter and the base period Tnep detected in step S1 is present in the control range Ttotal (see FIG. 8), then the condition ts≧tmax in step S6 is satisfied.

When the condition ts≧tmax in step S6 is satisfied, the sampling period ts calculated in step S6 is determined as the sampling period ts to be used in the present control cycle. Subsequently, as described above, the base signal generating means 22, the reference signal generating means 28, and the active control means 32 update the filter coefficients of the first adaptive notch filter 14*a* and the second adaptive notch filter 14*b*.

If the sampling period ts to be used in the present control cycle which is calculated in step S2 is of a value smaller than the noise canceling ability limit sampling period tmax in step S3, then the determination in step S3 becomes negative.

For an easier understanding of the control process, it is also assumed that the sampling period characteristic curve C used in the preceding control cycle is the sampling period characteristic curve C3 (the division number m3).

After the determination in step S3 becomes negative, it is determined in step S8 whether or not the sampling period ts to be used in the present control cycle which is calculated in step S2 is of a value equal to or smaller than the processing ability limit sampling period tmin.

If the sampling period ts is not of a value equal to or smaller than the processing ability limit sampling period tmin, then since the sampling period ts is present between the noise canceling ability limit sampling period tmax and the processing ability limit sampling period tmin, the sampling period characteristic curve C3 (the division number m3) is not changed, and the sampling period ts (ts=Tnep/m3) which is calculated in step S2 is determined to be the sampling period ts to be used in the present control cycle in step S7. Subsequently, as described above, the base signal generating means 22, the reference signal generating means 28, and the active control means 32 update the filter coefficients of the first adaptive notch filter 14*a* and the second adaptive notch filter 14*b*.

If the sampling period ts (ts=Tnep/m3) to be used in the present control cycle which is calculated in step S2, is of a value equal to or smaller than the processing ability limit sampling period tmin in step S8, e.g., if the vehicle is accelerating, i.e., if the base period Tnep is decreasing, and the presently detected base period Tnep is of a value smaller than the third identical division number lower limit base period TL3 as compared with the time when the sampling period ts was calculated in the preceding control cycle, then since the sampling period ts exceeds the range of the sampling period characteristic curve C3, the determination in step S8 becomes affirmative. In step S9, the division number m is then changed to change the sampling period characteristic curve C to a characteristic curve closer to the upper limit base period.

Inasmuch as the base period Tnep is of a value smaller than the third identical division number lower limit base period TL3, the division number m changes from the division number m3 to the division number m2, so that the sampling period characteristic curve C3 changes to the sampling period characteristic curve C2.

If the base period Tnep becomes shorter and the base period Tnep is of a value smaller than the second upper limit base period TU2 while the control process is being performed with the division number m1 on the sampling period characteristic curve C1, then the division number m changes from the division number m1 to the division number m3, and the sampling period characteristic curve C1 changes to the sampling period characteristic curve C3.

In step S10, the sampling period ts (ts=Tnep/m2) to be used in the present control cycle is calculated with the changed division number m2.

By thus calculating the sampling period ts with the division number m changed from the division number m3 to the division number m2, since the division numbers m2, m3 are related to each other according to m2<m3, if the sampling period ts becomes longer and the base period Tnep detected in step S1 is present in the control range Ttotal (see FIG. 8), then the condition ts≧tmin in step S11 is satisfied.

In step S7, the sampling period ts which is calculated in step S10 is determined to be the sampling period ts to be used in the present control cycle. Subsequently, as described above, the base signal generating means 22, the reference signal generating means 28, and the active control means 32 update the filter coefficients of the first adaptive notch filter 14*a* and the second adaptive notch filter 14*b*.

Figure 11:
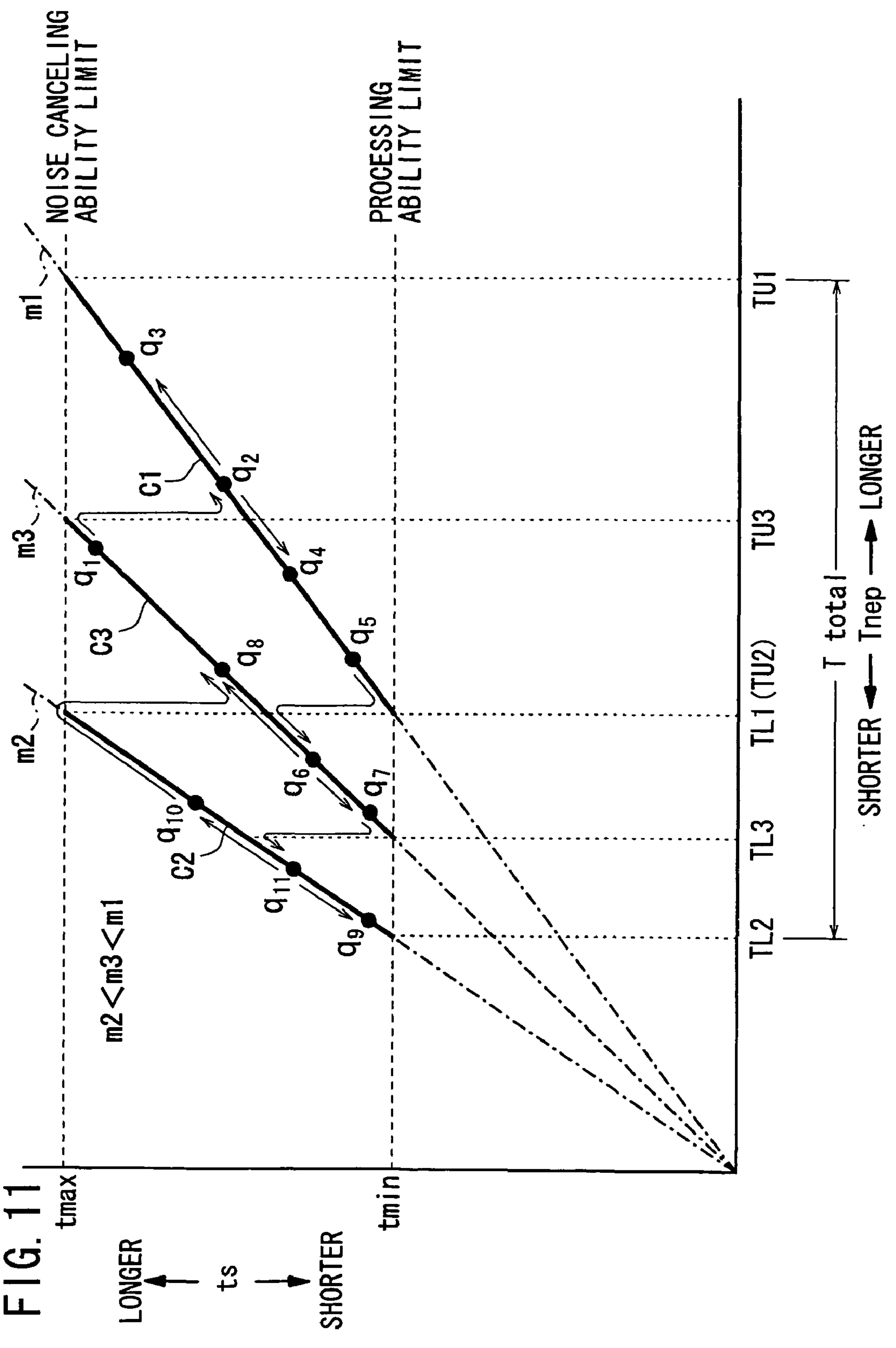
FIG. 11 is a diagram illustrative of a hysteresis control process according to the third embodiment.

The above processing sequence according to the flowchart shown in FIG. 10 will be described below with reference to FIG. 11.

In steps S1 through S6, the sampling period ts in the preceding control cycle is present in an operating point q1 (division number 3) indicated by the solid dot, and the vehicle is decelerated. If the sampling period ts calculated in the present control cycle is of a value greater than the noise canceling ability limit sampling period tmax, then the operating point moves from the operating point q1 on the sampling period characteristic curve C3 to an operating point q2 on the sampling period characteristic curve C1. If the vehicle is further decelerated, the operating point moves from the operating point q2 to an operating point q3 on the sampling period characteristic curve C1.

In steps S8 through S11, if the operating point q in the preceding control cycle is the operating point q3 and the vehicle is accelerated until the base period Tnep is of a value lower than the third upper limit base period TU3, then the operating point q moves to an operating point q4 on the same sampling period characteristic curve C1.

According to the above control process, when the operating point q moves from the operating point q1 to the operating point q2, even if the base period Tnep fluctuates, i.e., even if the engine rotational speed fluctuates, due to air-fuel combustion fluctuations in the engine, the operating point q does not go back to the operating point q1, but moves on the sampling period characteristic curve C1. Therefore, the division number m does not fluctuate, resulting in a smooth noise canceling control process.

Remaining details of the hysteresis operation shown in FIG. 11 will briefly be described below. If the vehicle is accelerated in the operating point q4 and the base period Tnep becomes smaller than the second upper limit base period TU2, then the operating point q moves to an operating point q6. If the vehicle is decelerated when the operating point q moves to the operating point q6, the operating point q goes to an operating point q8. If the acceleration is continued, the operating point q moves to an operating point q7. If the vehicle is further accelerated in the operating point 7, then when the base period Tnep becomes smaller than the third identical division number lower limit base period TL3, the operating point q moves to an operating point q11. Upon continued acceleration, the operating point q moves to an operating point q9. If the vehicle is decelerated, the operating point q goes from the operating point q9 to an operating point q10. If the vehicle is further decelerated, the operating point q goes from the operating point q10 to the operating point q8.

According to the third embodiment, in the active vibration noise control apparatus 10 operated by the process according to the second embodiment, as shown in FIG. 8, the sampling period calculating circuit 12 uses the base period Tnep of a particular base signal between the upper limit base period TU1 and the identical division number lower limit base period TL1 as the third upper limit base period TU3, determines the third division number m3 which is of a value produced when the third upper limit base period TU3 is divided by the upper limit sampling period tmax, uses a period produced when the lower limit sampling period tmin is multiplied by the third division number m3 as the third identical division number lower limit base period TL3, and outputs a value produced when the base period Tx3 of the base signal is divided by the third division number m3 as the third sampling period tx3 if the base period Tnep of the base signal is present in the range between the third upper limit base period TU3 and the third identical division number lower limit base period TL3.

The base signal generating means 22 uses the quotient produced when the predetermined number N is divided by the third division number m3 or the sum of the quotient and 1 as the third step number m3. If the base period Tnep of the base signal is present in the range between the third upper limit base period TU3 and the third identical division number lower limit base period TL3, then the base signal generating means 22 reads waveform data from the waveform data table 19 for each third step number P3 in the third sampling period tx3 to generate the base signal X.

When the vehicle is accelerated to reduce the base period Tnep, if the base period Tnep becomes smaller than the identical division number lower limit base period TL1, then the sampling period calculating circuit 12 switches from the sampling period tx to the third sampling period tx3 and outputs the third sampling period tx3. If the base period Tnep becomes smaller than the third identical division number lower limit base period TL3, then the sampling period calculating circuit 12 switches from the sampling period tx3 to the second sampling period tx2 and outputs the second sampling period tx2. When the vehicle is decelerated to increase the base period Tnep, if the base period Tnep becomes greater than the second upper limit base period TU2, then the sampling period calculating circuit 12 switches from the second sampling period tx2 to the third sampling period tx3 and outputs the third sampling period tx3. If the base period Tnep becomes greater than the third upper limit base period TU3, then the sampling period calculating circuit 12 switches from the third sampling period tx3 to the sampling period tx and outputs the sampling period tx.

At this time, since the third division number m3 is of a value greater than the second division number m2 and the first division number m1 is of a value greater than the third division number m3 (m2<m3<m1), if the sampling period ts calculated from the presently detected base period Tnep using the preceding division number m prior to the update is of a value greater than the noise canceling ability limit sampling period tmax, then the preceding division number m is changed to a division number m having a value greater by 1, and the present sampling period ts is calculated. If the sampling period ts calculated from the presently detected base period Tnep using the preceding division number m prior to the update is of a value smaller than the noise canceling ability limit sampling period tmin, then the preceding division number m is changed to a division number m having a value smaller by 1, and the present sampling period ts is calculated.

According to the third embodiment, even if the base period Tnep detected depending on noise contains fluctuations, since hysteresis is given when the division number m is changed, it is possible to continue the smooth noise control process.

Specifically, if the operating point moves from the operating point q1 to the operating point q2 while the vehicles is being decelerated, then hysteresis is given. Consequently, a smooth noise control process is possible even if the base period Tnep detected depending on noise contains fluctuations. As the division numbers m1 through m3 are a real number, the freedom of design is increased. As a result, less strict limits are posed on the processing ability of a CPU for achieving a wider control range Ttotal.

4th Embodiment

Figure 12:
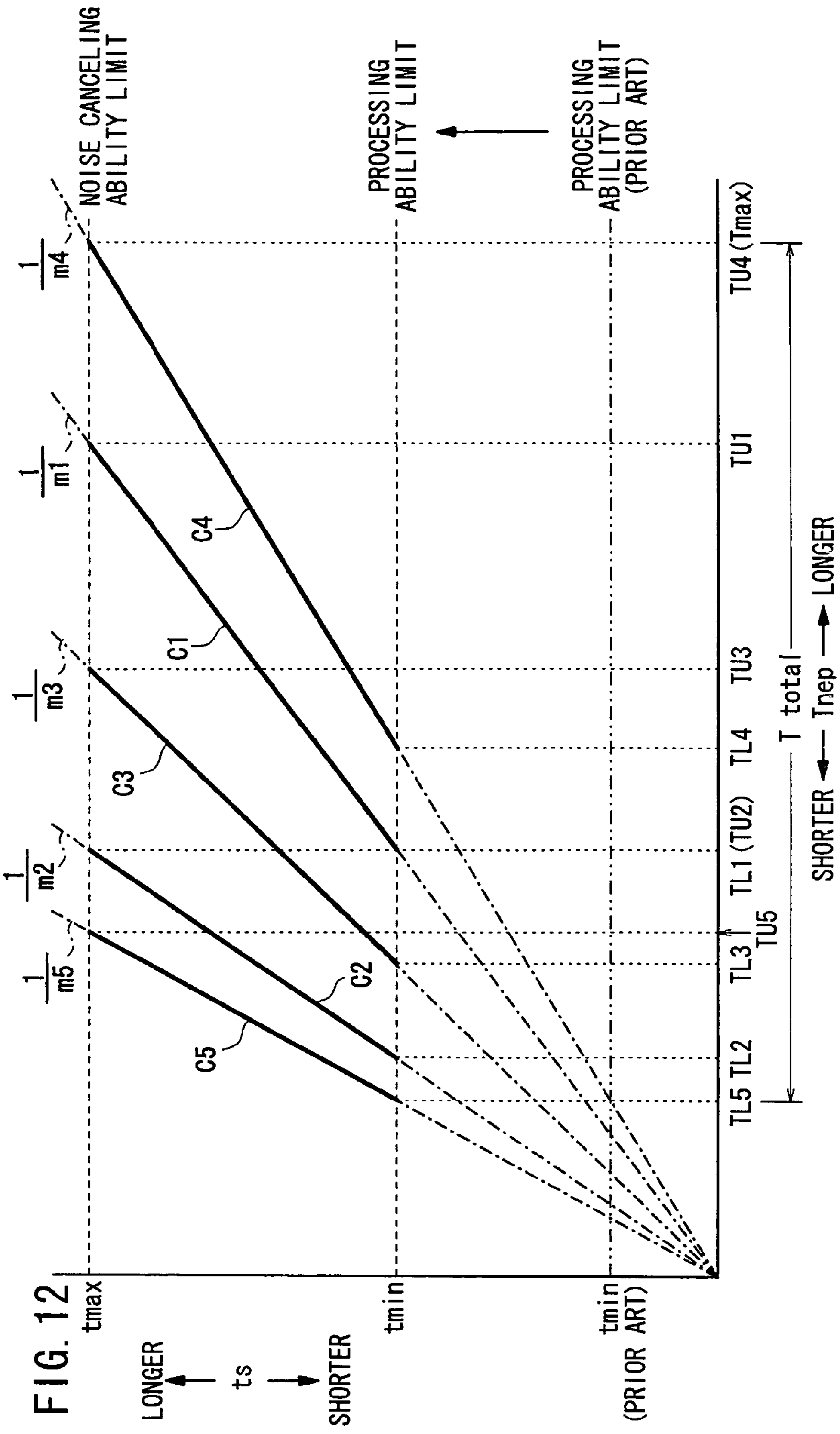
FIG. 12 is a diagram illustrative of the manner in which the control range is further widened according to a fourth embodiment of the present invention.

As shown in FIG. 12, if the sampling period ts is present between the noise canceling ability limit sampling period tmax and the processing ability limit sampling period tmin, and the control range Ttotal for the base period Tnep is to be widened, then a fourth upper limit base period TU4, i.e. the upper limit base period Tmax of the control range Ttotal, and a sampling period characteristic curve C4 of a division number m4 in a fourth identical division number lower limit base period TL4 may be introduced, and a fifth upper limit base period TU5 and a sampling period characteristic curve C5 of a division number m5 in a fifth identical division number lower limit base period TL5 may be introduced (m5<m2<m3<m1<m4).

Figure 13:
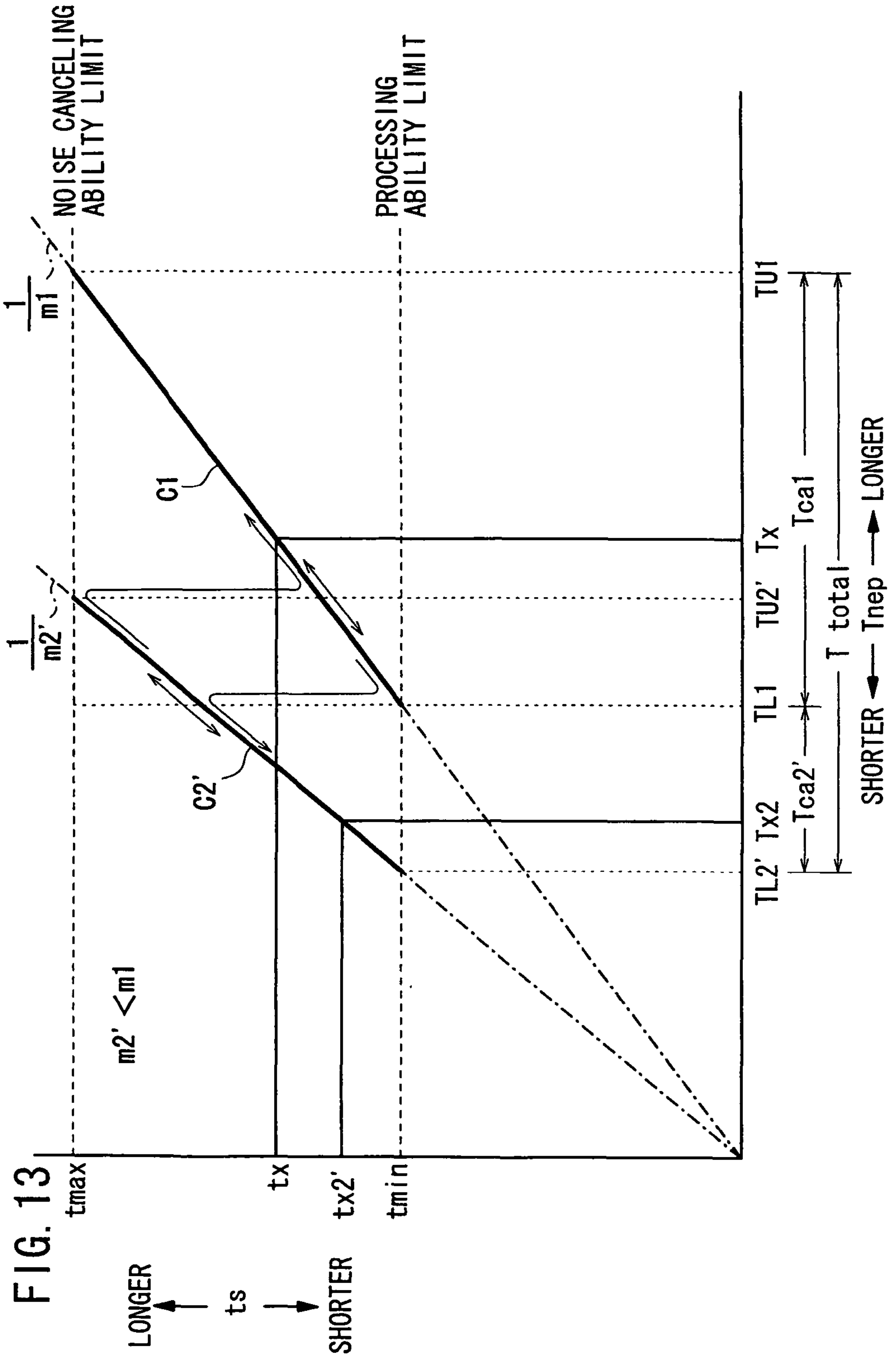
FIG. 13 is a diagram illustrative of a modification related to the second embodiment and the third embodiment.

In this manner, as can be seen from FIG. 12 which includes the CPU processing ability limit sampling period tmin shown in FIG. 17, noise control can be achieved in the same control range Ttotal even if the processing ability of the CPU is lowered, or in other words, even if a CPU having a low processing ability and a low cost is employed. Modification of the second and third embodiments:

The present invention also covers a modification shown in FIG. 13 as can be seen from the second embodiment shown in FIG. 6 and the third embodiment shown in FIG. 8.

Specifically, if the control range Ttotal is wider than a range between the upper limit base period TU1 and the identical division number lower limit base period TL1 and has a lower limit base period lower than the identical division number lower limit base period TL1, then the sampling period calculating circuit 12 uses the base period Tnep of a particular base signal which is smaller than the upper limit base period TU1 and greater than the identical division number lower limit base period TL1 on the sampling frequency characteristic curve C1 as a second upper limit base period TU2', determines a second division value m2' which is of a value produced when a second upper limit base period TU2' is divided by the upper limit sampling period tmax, uses a period produced when the lower limit sampling period TL1 is multiplied by the second division number m2' as a second identical division number lower limit base period TL2', and outputs a value produced when the base period Tx2 of the base signal X is divided by the second division number m2' as a second sampling period tx2' if the base period Tnep of the base signal X is in a range corresponding to a sampling characteristic curve C2' in a range between the second upper limit base period TU2' and the second identical division number lower limit base period TL2'.

The base signal generating means 22 uses the quotient produced when the predetermined number N is divided by the second division number m2' or the sum of the quotient and 1 as the second step number P2'. If the base period Tnep of the base signal X is present in the second range between the second upper limit base period TU2' and the second identical division number lower limit base period TL2', then the base signal generating means 22 reads waveform data from the waveform data table 19 for each second step number P2' in the second sampling period tx2' to generate the base signal X.

In this manner, the control range can be widened without having to shorten the processing ability limit sampling period tmin.

When the base period Tnep of the base signal X changes to a smaller value, if the base period Tnep of the base signal X becomes smaller than the identical division number lower limit base period TL1, then the sampling period calculating circuit 12 changes from the sampling period tx (sampling characteristic curve C1) to the second sampling period tx2' (sampling characteristic curve C2') and outputs the second sampling period tx2'. When the base period Tnep of the base signal X changes to a greater value, if the base period Tnep of the base signal X becomes greater than the second upper limit base period TU2', then the sampling period calculating circuit 12 changes from the second sampling period tx2' to the sampling period tx and outputs the sampling period tx.

According to the present modification, even if the base period Tnep of the base signal X detected depending on noise contains fluctuations, since hysteresis is given when the division number m is changed between the division numbers m1, m2, it is possible to perform a noise control process for a smooth noise canceling capability.

The active vibration noise control apparatus 10 as it is incorporated in a vehicle will be described in specific detail below with reference to FIG. 14.

Figure 14:
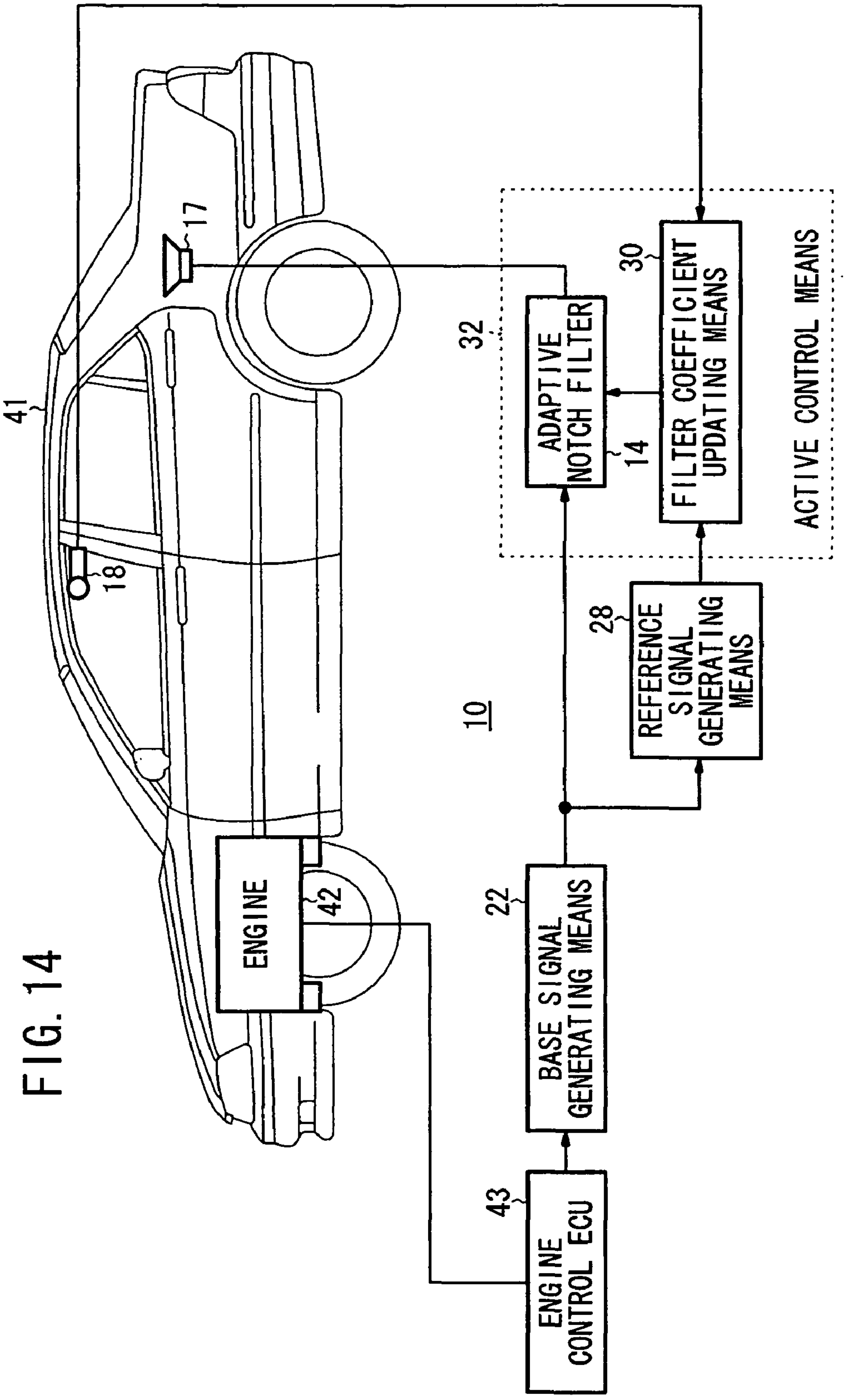
FIG. 14 is a block diagram of the active vibration noise control apparatus according to an embodiment of the present invention as it is incorporated in a vehicle.
Figure 15:
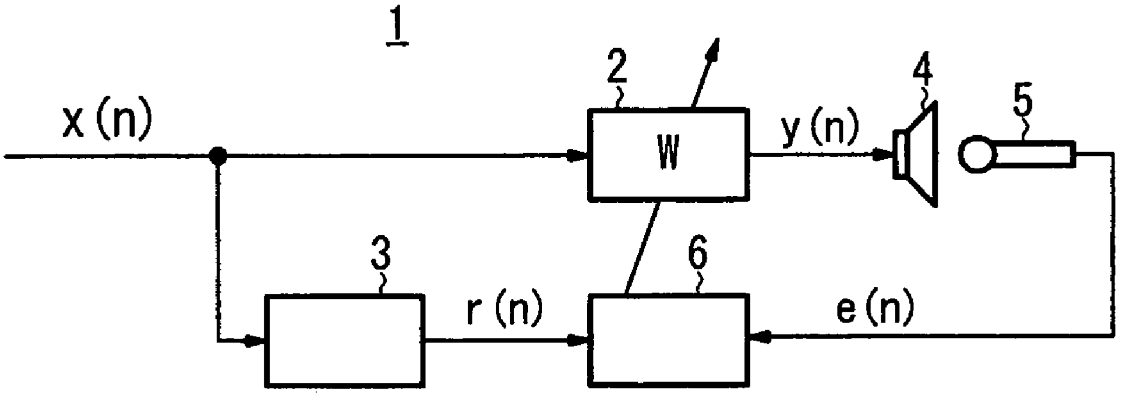
FIG. 15 is a block diagram showing an electric arrangement of a general active vibrational noise control apparatus.
Figure 16:
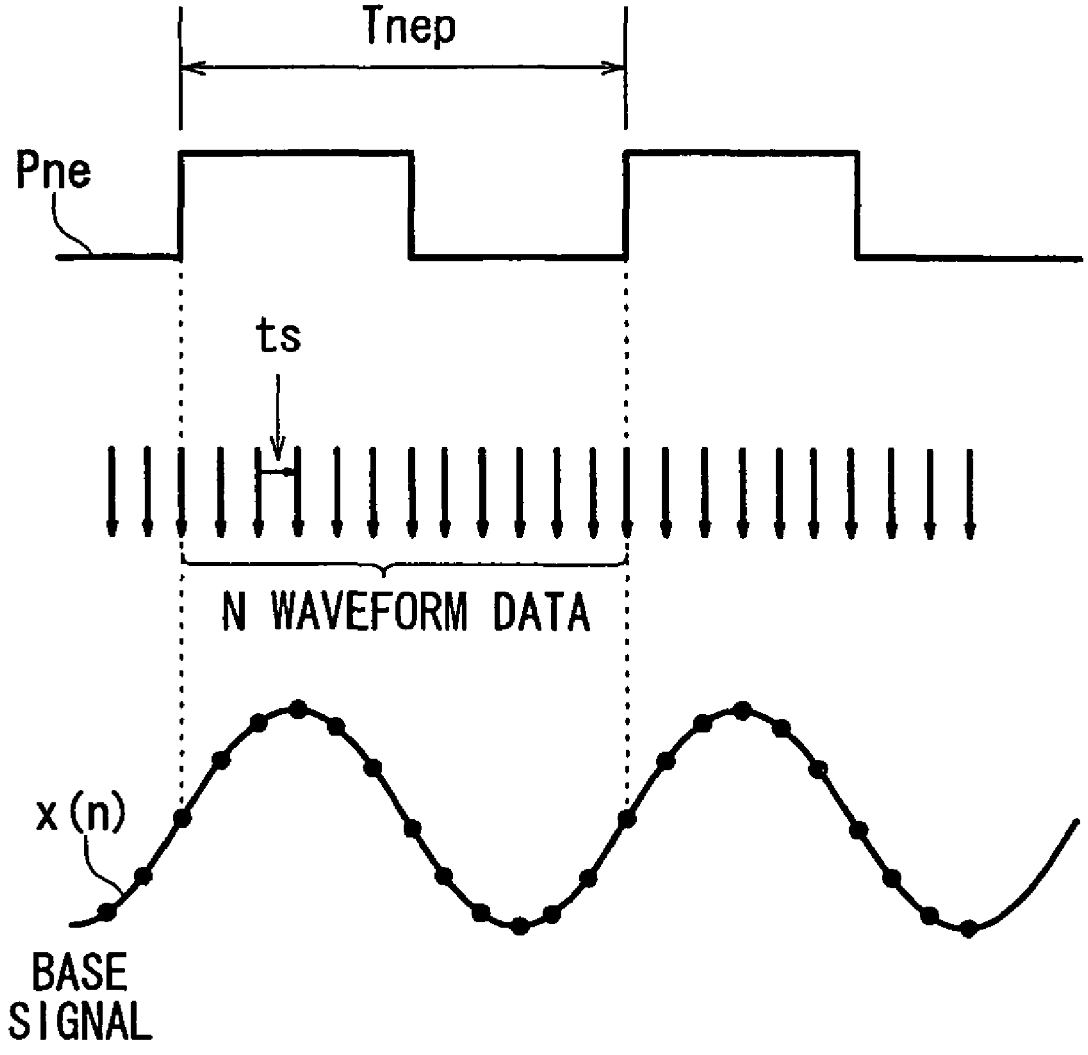
FIG. 16 is a diagram illustrative of the conventional variable sampling technology (synchronous sampling technology)

FIG. 14 schematically shows an arrangement in which the active vibration noise control apparatus 10 with one microphone is incorporated in a vehicle 41 for canceling noise including the muffled sound in the passenger compartment of the vehicle.

The speaker 17 is disposed in a given position behind rear seats in the passenger compartment of the vehicle 41. The microphone 18 is mounted on a central portion of the ceiling of the passenger compartment. Alternatively, the microphone 18 may be mounted in the instrumental panel in the passenger compartment.

In FIG. 14, the active vibration noise control apparatus 10 has its major part constructed in the form of a microcomputer having a low processing ability and a low cost.

As shown in FIG. 14, the active vibration noise control apparatus 10 has the base signal generating means 22, the reference signal generating means 28, and the active control means 32 including the adaptive notch filter 14 (14*a*, 14*b*) and the filter coefficient updating means 30 (30*a*, 30*b*). The D/A converter 17*a*, the low-pass filter 17*b*, the amplifiers 17*c*, 18*a*, the bandpass filter 18*b*, and the A/D converter 18*c* are omitted from illustration.

The vehicle 41 has an engine 42 controlled by an engine control ECU (engine controller) 43. Engine pulses output from the engine control ECU 43 are supplied to the active vibration noise control apparatus 10 which operates in cooperation with the speaker 17 and the microphone 18. The speaker 17 is driven by an output signal from the adaptive notch filter 14 which is adaptively controlled to minimize the output signal from the microphone 18, for thereby canceling noise in the passenger compartment which is generated by vibrational noise of the engine 42. The noise canceling process has been described in detail above with respect to the active vibration noise control apparatus 10 shown in FIG. 1.

Although certain preferred embodiments of the present invention have been shown and described in detail, it should be understood that various changes and modifications may be made therein without departing from the scope of the appended claims.

What is claimed is:

1. An active vibration noise control apparatus comprising:
a control sound source for generating control sound in a space in which noise is transmitted from a noise source;
frequency detecting means for detecting a noise generating state of said noise source and outputting a harmonic base frequency selected from frequencies of the noise generated by the noise source and a base period corresponding to said base frequency;
residual noise detecting means for detecting residual noise at a predetermined position in said space; and
active control means for driving said control sound source to reduce the noise in said space based on a base signal and said residual noise;
said active control means comprising:
a waveform data table for storing waveform data of a sine wave or a cosine wave discretized into a predetermined number of values;
sampling period calculating means for calculating a sampling period based on said base period; and
base signal generating means for reading the waveform data from said waveform data table and generating said base signal;
wherein said sampling period calculating means:
uses the base period of a particular base signal in a control range as an upper limit base period, and determines a division number which is a value produced when said upper limit base period is divided by an upper limit sampling period which is necessary for said active control means to provide a noise canceling capability;
uses a period produced when a lower limit sampling period which is a limit of a processing capability of said active control means is multiplied by said division number, as an identical division number lower limit base period; and
if the base period of said base signal is present in a range between said upper limit base period and said identical division number lower limit base period, outputs a value produced when the base period of the base signal is divided by said division number as said sampling period; and
wherein said base signal generating means:
uses the quotient produced when said predetermined number is divided by said division number or the sum of said quotient and 1 as a step number, and reads the waveform data from said waveform data table for each said step number in a sampling period which is of a value produced when said base period of said base signal is divided by said division number, thereby to generate said base signal.

2. An active vibration noise control apparatus according to claim 1, wherein said base period of said particular base signal comprises a longest base period in said control range.

3. An active vibration noise control apparatus according to claim 1, wherein if said control range is wider than a range from said identical division number lower limit base period to said upper limit base period and has a lower limit base period smaller than said identical division number lower limit base period, said sampling period calculating means:
uses said identical division number lower limit base period as a second upper limit base period, determines a second division number which is of a value produced when said second upper limit base period is divided by said upper limit sampling period, uses a period produced when said lower limit sampling period is multiplied by said second division number as a second identical division number lower limit base period, and outputs a value produced when the base period of said base signal is divided by said second division number as a second sampling period if the base period of said base signal is present in a range between said second upper limit base period and said second identical division number lower limit base period; and
wherein said base signal generating means:
uses the quotient produced when said predetermined number is divided by said second division number or the sum of said quotient and 1 as a second step number, and reads the waveform data from said waveform data table for each said second step number in said second sampling period, thereby to generate said base signal, if the base period of said base signal is present in a second range between said second upper limit base period and said second identical division number lower limit base period.

4. An active vibration noise control apparatus according to claim 2, wherein if said control range is wider than a range from said identical division number lower limit base period to said upper limit base period and has a lower limit base period smaller than said identical division number lower limit base period, said sampling period calculating means:
uses said identical division number lower limit base period as a second upper limit base period, determines a second division number which is of a value produced when said second upper limit base period is divided by said upper limit sampling period, uses a period produced when said lower limit sampling period is multiplied by said second division number as a second identical division number lower limit base period, and outputs a value produced when the base period of said base signal is divided by said second division number as a second sampling period if the base period of said base signal is present in a range between said second upper limit base period and said second identical division number lower limit base period; and wherein said base signal generating means:

uses the quotient produced when said predetermined number is divided by said second division number or the sum of said quotient and 1 as a second step number, and reads the waveform data from said waveform data table for each said second step number in said second sampling period, thereby to generate said base signal, if the base period of said base signal is present in a second range between said second upper limit base period and said second identical division number lower limit base period.

5. An active vibration noise control apparatus according to claim 3, wherein said sampling period calculating means:

uses the base period of a particular base signal between said upper limit base period and said identical division number lower limit base period as a third upper limit base period, determines a third division number which is of a value produced when said third upper limit base period is divided by said upper limit sampling period, uses a period produced when said lower limit sampling period is multiplied by said third division number as a third identical division number lower limit base period, and outputs a value produced when the base period of said base signal is divided by said third division number as a third sampling period if the base period of said base signal is present in a range between said third upper limit base period and said third identical division number lower limit base period;

wherein said base signal generating means:

uses the quotient produced when said predetermined number is divided by said third division number or the sum of said quotient and 1 as a third step number, and reads the waveform data from said waveform data table for each said third step number in said third sampling period, thereby to generate said base signal, if the base period of said base signal is present in a third range between said third upper limit base period and said third identical division number lower limit base period; and wherein when the base period of said base signal changes to a smaller value, if said base period becomes smaller than said identical division number lower limit base period, then said sampling period calculating means changes from said sampling period to said third sampling period and outputs said third sampling period, and if said base period becomes smaller than said third identical division number lower limit base period, then said sampling period calculating means changes from said third sampling period to said second sampling period and outputs said second sampling period, and when the base period of said base signal changes to a greater value, if said base period becomes greater than said second upper limit base period, then said sampling period calculating means changes from said second sampling period to said third sampling period and outputs said third sampling period, and if said base period becomes greater than said third upper limit base period, then said sampling period calculating means changes from said third sampling period to said sampling period and outputs said sampling period.

6. An active vibration noise control apparatus according to claim 4, wherein said sampling period calculating means:

uses the base period of a particular base signal between said upper limit base period and said identical division number lower limit base period as a third upper limit base period, determines a third division number which is of a value produced when said third upper limit base period is divided by said upper limit sampling period, uses a period produced when said lower limit sampling period is multiplied by said third division number as a third identical division number lower limit base period, and outputs a value produced when the base period of said base signal is divided by said third division number as a third sampling period if the base period of said base signal is present in a range between said third upper limit base period and said third identical division number lower limit base period;

wherein said base signal generating means:

uses the quotient produced when said predetermined number is divided by said third division number or the sum of said quotient and 1 as a third step number, and reads the waveform data from said waveform data table for each said third step number in said third sampling period, thereby to generate said base signal, if the base period of said base signal is present in a third range between said third upper limit base period and said third identical division number lower limit base period; and wherein when the base period of said base signal changes to a smaller value, if said base period becomes smaller than said identical division number lower limit base period, then said sampling period calculating means changes from said sampling period to said third sampling period and outputs said third sampling period, and if said base period becomes smaller than said third identical division number lower limit base period, then said sampling period calculating means changes from said third sampling period to said second sampling period and outputs said second sampling period, and when the base period of said base signal changes to a greater value, if said base period becomes greater than said second upper limit base period, then said sampling period calculating means changes from said second sampling period to said third sampling period and outputs said third sampling period, and if said base period becomes greater than said third upper limit base period, then said sampling period calculating means changes from said third sampling period to said sampling period and outputs said sampling period.

7. An active vibration noise control apparatus according to claim 1, wherein if said control range is wider than a range from said identical division number lower limit base period to said upper limit base period and has a lower limit base period smaller than said identical division number lower limit base period, said sampling period calculating means:

uses the base period of a particular base signal which is smaller than said upper limit base period and greater than said identical division number lower limit base period as a second upper limit base period, determines a second division number which is of a value produced when said second upper limit base period is divided by said upper limit sampling period, uses a period produced when said lower limit sampling period is multiplied by said second division number as a second identical division number lower limit base period, and outputs a value produced when the base period of said base signal is divided by said second division number as a second sampling period if the base period of said base signal is present in a range between said second upper limit base period and said second identical division number lower limit base period; and wherein said base signal generating means:

uses the quotient produced when said predetermined number is divided by said second division number or the sum of said quotient and 1 as a second step number, and reads the waveform data from said waveform data table for each said second step number in said second sampling period, thereby to generate said base signal, if the base period of said base signal is present in a second range between said second upper limit base period and said second identical division number lower limit base period.

8. An active vibration noise control apparatus according to claim 2, wherein if said control range is wider than a range from said identical division number lower limit base period to said upper limit base period and has a lower limit base period smaller than said identical division number lower limit base period, said sampling period calculating means:

uses the base period of a particular base signal which is smaller than said upper limit base period and greater than said identical division number lower limit base period as a second upper limit base period, determines a second division number which is of a value produced when said second upper limit base period is divided by said upper limit sampling period, uses a period produced when said lower limit sampling period is multiplied by said second division number as a second identical division number lower limit base period, and outputs a value produced when the base period of said base signal is divided by said second division number as a second sampling period if the base period of said base signal is present in a range between said second upper limit base period and said second identical division number lower limit base period; and wherein said base signal generating means:

uses the quotient produced when said predetermined number is divided by said second division number or the sum of said quotient and 1 as a second step number, and reads the waveform data from said waveform data table for each said second step number in said second sampling period, thereby to generate said base signal, if the base period of said base signal is present in a second range between said second upper limit base period and said second identical division number lower limit base period.

9. An active vibration noise control apparatus according to claim 7, wherein when the base period of said base signal changes to a smaller value, if said base period becomes smaller than said identical division number lower limit base period, then said sampling period calculating means changes from said sampling period to said second sampling period and outputs said second sampling period, and when the base period of said base signal changes to a greater value, if said base period becomes greater than said second upper limit base period, then said sampling period calculating means changes from said second sampling period to said sampling period and outputs said sampling period.

10. An active vibration noise control apparatus according to claim 8, wherein when the base period of said base signal changes to a smaller value, if said base period becomes smaller than said identical division number lower limit base period, then said sampling period calculating means changes from said sampling period to said second sampling period and outputs said second sampling period, and when the base period of said base signal changes to a greater value, if said base period becomes greater than said second upper limit base period, then said sampling period calculating means changes from said second sampling period to said sampling period and outputs said sampling period.

* * * * *